United States Patent
Blumrich et al.

(10) Patent No.: US 10,386,297 B2
(45) Date of Patent: Aug. 20, 2019

(54) METHOD AND APPARATUS FOR EXAMINING AN ELEMENT OF A PHOTOLITHOGRAPHIC MASK FOR THE EUV RANGE

(71) Applicant: Carl Zeiss SMT GmbH, Oberkochen (DE)

(72) Inventors: Jörg Frederik Blumrich, Jena (DE); Johannes Ruoff, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 15/838,699

(22) Filed: Dec. 12, 2017

(65) Prior Publication Data
US 2018/0164207 A1    Jun. 14, 2018

(30) Foreign Application Priority Data
Dec. 12, 2016    (DE) .................. 10 2016 224 690

(51) Int. Cl.
*G01N 21/33* (2006.01)
*G01N 21/956* (2006.01)

(52) U.S. Cl.
CPC ........... *G01N 21/33* (2013.01); *G01N 21/956* (2013.01); *G01N 2021/95676* (2013.01)

(58) Field of Classification Search
CPC ....... G01N 2021/95676; G01N 21/956; G01N 21/33
See application file for complete search history.

(56) References Cited

U.S. PATENT DOCUMENTS

| | | | |
|---|---|---|---|
| 6,235,434 B1 | 5/2001 | Sweeney et al. | |
| 8,142,958 B2 | 3/2012 | Holfeld | |
| 8,739,098 B1 | 5/2014 | Clifford et al. | |
| 10,060,947 B2* | 8/2018 | Budach | G03F 1/22 |
| 2009/0297988 A1* | 12/2009 | Tanaka | B82Y 10/00 430/319 |
| 2017/0176851 A1 | 6/2017 | Peters et al. | |

FOREIGN PATENT DOCUMENTS

| | | | |
|---|---|---|---|
| DE | 102007028172 | 12/2008 | ............... G03F 1/08 |
| DE | 102011079382 | 1/2013 | ............... G03F 1/72 |
| DE | 102014214257 | 1/2016 | ............ G01B 11/24 |
| EP | 1 829 052 | 4/2008 | ............... G21K 1/06 |

(Continued)

OTHER PUBLICATIONS

Pang et al., "Compensation for EUV multilayer defects within arbitrary layouts by absorber pattern modification", "Extreme Ultraviolet Lithography", edited by B.M. La Fontaine, P.P. Naulleau, Proc. of SPIE, vol. 7969, pp. 79691E-1-79691E-14 (Mar. 2011).

(Continued)

*Primary Examiner* — David P Porta
(74) *Attorney, Agent, or Firm* — Fish & Richardson P.C.

(57) ABSTRACT

The present application relates to a method for examining at least one element of a photolithographic mask for an extreme ultraviolet (EUV) wavelength range, wherein the method includes the steps of: (a) examining the at least one element with light in the EUV wavelength range; and (b) determining the behavior of the at least one element in the EUV wavelength range.

20 Claims, 15 Drawing Sheets

(56) References Cited

FOREIGN PATENT DOCUMENTS

| WO | WO 00/34828 | 6/2000 | ............... | G03F 1/00 |
|---|---|---|---|---|
| WO | WO 2011/161243 | 12/2011 | ............... | G03F 1/14 |
| WO | WO 2013/010976 | 1/2013 | ............... | G03F 1/22 |
| WO | WO 2015/144700 | 10/2015 | | |
| WO | WO 2016/037851 | 3/2016 | ............... | G03F 1/72 |

OTHER PUBLICATIONS

Pang et al., "EUV multilayer defect compensation (MDC) by absorber pattern modification—From theory to wafer validation" in *Photomask Technology 2011*, edited by,W. Maurer, F.E. Abboud, Proc. of SPIE, vol. 8166, pp. 81662E-1-81662E-15 (2011).

Waiblinger et al., "The door opener for EUV mask repair", "*Photomask and Next Generation Lithography Mask Technology XIX*", Proc. of SPIE, vol. 8441, pp. 84410F-1-84410F-10 (2012).

German Office Action for German Application No. 10 2016 224 690.9 dated Jul. 25, 2017 (8 pages).

\* cited by examiner

+ Defocussing (over focussing)

Focus

− Defocussing (underfocussing)

METHOD AND APPARATUS FOR EXAMINING AN ELEMENT OF A PHOTOLITHOGRAPHIC MASK FOR THE EUV RANGE

CROSS-REFERENCE TO RELATED APPLICATIONS

This application claims the benefit of the German patent application DE 10 2016 224 690.9, entitled "Verfahren und Vorrichtung zum Untersuchen eines Elements einer photolithographischen Maske für den EUV-Bereich," and filed with the German Patent and Trademark Office on Dec. 12, 2016. The entire content of the above application is hereby incorporated by reference.

TECHNICAL FIELD

The present invention relates to a method and an apparatus for examining an element of a photolithographic mask for an extreme ultraviolet (EUV) wavelength range. Further, the invention relates to a method and an apparatus for compensating a defect of a mask for the EUV wavelength range.

BACKGROUND

As a consequence of the growing integration density in the semiconductor industry, photolithography masks have to image increasingly smaller structures on wafers. In order to take account of this trend, the exposure wavelength of lithography apparatuses is being shifted to ever shorter wavelengths. Future lithography systems will probably operate with wavelengths in the extreme ultraviolet (EUV) range (preferably but not necessarily in the range of 6 nm to 15 nm). The EUV wavelength range places huge demands on the precision of optical elements in the beam path of future lithography systems. In all probability, the optical elements, and hence also the photolithographic masks, will be reflective optical elements.

EUV mirrors comprise a substrate exhibiting little thermal expansion. A multilayer structure comprising, for example, approximately 20 to approximately 80 double layers comprising silicon (Si) and molybdenum (Mo), or other suitable materials, is applied to the substrate, said layers acting as a dielectric mirror. The European patent document EP 1 829 052 B1 discloses a possible exemplary embodiment of such a reflective multilayer system for the EUV wavelength range.

EUV photolithography masks, or simply EUV masks, additionally have an absorber structure made of absorbing pattern elements on the multilayer structure. In the regions of the EUV mask covered by pattern elements of the absorber structure, incident EUV photons are absorbed or at least not reflected like in the other regions.

EUV masks—or, in general, photomasks—are projection templates, the most important application of which is photolithography for producing semiconductor elements, in particular integrated circuits. Photomasks must be largely error-free, since an error of the mask would reproduce on each wafer during each exposure. Therefore, the highest demands in respect of planar qualities, cleanliness, temperature stability, reflection constancy and freedom of errors are placed on the materials of the optical elements for the EUV range, in particular the photomasks.

In the case of a photomask, it is important that the pattern elements of the absorber structure on the photomask exactly image the structure elements predetermined by the design of the semiconductor element into the photoresist on the wafer. The intended dimension of the structure elements produced in the photoresist by the absorber pattern is referred to as a critical dimension (CD). This variable, or the variation thereof, is an essential characteristic for the quality of a photomask. Freedom of errors for photomasks means that, in this context, the mask upon exposure with the actinic wavelength images an intended dimension within a predetermined error interval onto a wafer, i.e. the CD may only vary within the predetermined error interval. If this condition is satisfied, the photomask has no visible defects or printable defects on a wafer.

Currently, it is not possible to produce substrates and/or multilayer structures for photomasks for the EUV wavelength range which are free from printable defects or errors. The defects considered in this application may have their origin in small local unevenness of the mask substrate (<10 nm deviation from a predetermined thickness), which may propagate through the multilayer structure. Further, local defects within the multilayer structure or particles on the substrate or within the multilayer structure are the cause of impairments of the function of the multilayer structure as a mirror. Below, these defects are referred to as buried defects or defects of the multilayer structure—as is conventional in the art. Currently, there are various concepts for avoiding or at least attenuating the effect of printable defects of EUV masks, which are caused by defects in the multilayer structure.

Thus, after examining the defects of a mask blank, i.e. a substrate with an applied multilayer structure, the pattern elements of the absorber structure can be arranged on the mask blank in such a way that the elements of the absorber pattern substantially cover the printable defects. The article "EUV multilayer defect compensation (MDC) by absorber pattern modification—From theory to wafer validation" by L. Peng, P. Hu, M. Satake, V. Tolani, D. Peng, Y. Li and D. Chen, in "Photomask Technology 2011," edited by W. Maurer, F. E. Abboud, Proc. of SPIE, Vol. 8166, 81662E-1-81662E-15, describes a simulation tool, with the aid of which the best possible arrangement of an absorber pattern on a defect-afflicted mask blank can be determined very quickly. However, above a certain defect density and depending on the structure of the absorbing pattern elements, this concept quickly reaches its limits.

The obvious procedure for rectifying a buried defect would be to remove the multilayer structure above the defect in a first step, remove the exposed defect in a second step and, thereupon, re-apply the part of the removed multilayer structure in a final step. In practice, this process cannot be carried out on account of the multiplicity of layers in the multilayer structure and the low thickness thereof of approximately 3 nm for the molybdenum (Mo) layers and approximately 4 nm for the silicon (Si) layers and the high demands on the planar properties of the layers or the interfaces thereof.

Instead, U.S. Pat. No. 6,235,434 B1 discloses a method of compensating the amplitude portion of a buried defect by modifying the pattern elements of the absorber structure of an EUV mask in the vicinity of a buried defect. Below, this process is referred to as "compensational repair." FIG. 1 schematically illustrates the mode of action thereof. A local reduction in the reflectivity which is caused by the locally disturbed surface of a buried defect is compensated by removing parts of the absorber material of adjacent pattern elements of the defect.

The aforementioned patent document describes that it is not the geometric dimension of the buried defect that is intended to be compensated, but its equivalent dimension. The equivalent dimension of a buried defect depends on its spatial orientation in relation to adjacent pattern elements and increases the further the defect is spaced apart from the closest pattern element. Phase defects have a smaller equivalent area than amplitude defects. The position and the equivalent dimension of defect-induced reflection disturbances can be determined by a characterization technique, such as e.g. lithographic printing.

By way of example, the compensational repair is likewise explained in the publication "Compensation for EUV multilayer defects within arbitrary layouts by absorber pattern modification" by L. Pang, C. Clifford, D. Peng, Y. Li, D. Chen, M. Satake, V. Tolani and L. He, in "Extreme Ultraviolet Lithography," edited by B. M. La Fontaine, P. P. Naulleau, Proc. of SPIE, Vol. 7969, 79691E-1-79691E-14. The modifications of the pattern elements of the absorber structure for compensating local pits or bumps of a mask blank, which are required for defect compensation, are determined with the aid of a simulation tool.

WO 00/34828 describes the repair of amplitude and phase defects of EUV masks on the basis of a change in the pattern elements in the vicinity of the defects.

U.S. Pat. No. 8,739,098 describes a simulation method for determining the dimensions of buried defects of EUV masks and the application of a "compensational repair" for repairing the buried defects.

WO 2016/037851 proposes the subdivision of defects of mask blanks into two classes, wherein the defects of the first class are covered by pattern elements of the absorber structure and the defects of the second class are at least attenuated by the above-described compensational repair.

The article "The door opener for EUV mask repair" by M. Waiblinger, R. Jonckheere, T. Bret, D. van den Heuvel, C. Baur and G. Baralia, in "Photomask and Next Generation Lithography Mask Technology XIX," edited by K. Kato, Proc. of SPIE, Vol. 84441, 84410F1-84410E-10, 2012, describes the repair of both defects of the absorbing pattern elements and also defects of the multilayer structure of EUV masks, wherein the last-mentioned defects are repaired with the aid of the compensational repair technique.

Further, WO 2011/161243 describes the compensation of defects of EUV masks by producing local changes in the multilayer structure of an EUV mask with the aid of an electron beam.

Moreover, WO 2013/010976 describes the correction of buried defects of EUV masks, wherein the defects are localized by the combined use of an ultraviolet radiation source, a scanning probe microscope and a scanning particle microscope.

Moreover, a further method uses ultrashort laser pulses for local compression of the substrate material of a photomask or mask blank for the purposes of compensating defects of EUV masks. WO 2015/144700 describes the introduction of pixels into a substrate of an EUV mask through the rear side of the substrate, i.e. the side of the mask substrate which lies opposite the multilayer structure.

Finally, in the article "Through-focus EUV multilayer defect repair with nanomachining," in "Extreme Ultraviolet (EUV) Lithography IV," edited by P. P. Naulleau, Proc. of SPIE, Vol. 8679, 86791I-1-86791I-4, G. McIntyre, E. Gallagher, T. Robinson, A. C. Smith, M. Lawliss, J. LeClaire, R. Bozak, R. White and M. Archuletta describe that, by way of compensation of the phase disturbances of the multilayer structure induced by local bumps or pits by use of a local removal of part of the defect (in the case of a local bump) or a local deposition of the material on the defect present in the form of a local pit, it is possible to compensate the phase error of these defects.

Defects of the multilayer structure currently represent a main obstacle for the use of photolithography in the EUV wavelength range. Despite the multiplicity of employed methods for correcting defects or attenuating defects, buried defects or defects of the multilayer structure of EUV masks often still cannot be repaired with the required quality.

Moreover, for the purposes of analyzing an EUV mask, it is very important that measurement tools facilitating the reliable determination of the behavior or the operational behavior of an EUV mask are available, without having to carry out time-consuming and expensive exposures of wafers. This point is relevant, in particular, against the background of the further development of EUV masks.

The present invention is therefore based on the problem of specifying methods and apparatuses which improve the examination of EUV masks and thereby also facilitate an improved compensation of defects of EUV masks.

The information provided above is merely to assist the reader in understanding the background of the invention. Some of the information provided in this "Background" section may not be prior art to the invention.

SUMMARY

According to one aspect of the present invention, the problem mentioned above is solved by a method for examining at least one element of a photolithographic mask for an extreme ultraviolet (EUV) wavelength range. In one embodiment, the method includes the steps of: (a) examining the at least one element with light in the EUV wavelength range; and (b) determining the behaviour of the at least one element upon irradiation with light in the EUV wavelength range.

For examining an element of a photolithographic mask for the EUV wavelength range (or, briefly, an EUV mask), a method according to the invention uses radiation which lies in the region of the actinic wavelength of the EUV mask. As a result, it is possible to directly measure the structure elements of an EUV mask, which are designed for the actinic wavelength, and directly determine the deviations from a predetermined intended dimension by experiment.

The at least one element may comprise at least one member from the group: at least one defect of a photolithographic mask, at least one critical point of a photolithographic mask and at least one component and/or at least part of a component of a photolithographic mask.

A method according to the invention can be used for analyzing a defect of an EUV mask. In addition to the analysis of the buried defects, which are predominantly described in this application, it is also possible to examine all further defects of EUV masks. This applies, in particular, to the experimental determination of defects of the absorber structure or defects of a phase-shifting structure.

In addition to examining a defect of an EUV mask, a method according to the invention can also be used for examining a critical point of a photolithographic mask for the EUV wavelength range. A defect has a parameter value above a defect threshold whereas a critical point has a parameter value that lies only just below the defect threshold. Hence, critical points of a photolithographic masks are points whose parameters meet the specification but wherein at least one parameter of a critical point comes close to the corresponding defect threshold. As explained in detail below, a method according to the invention allows the quantitative determination of a defect.

Further, a method according to the invention opens up new possibilities for reliably analyzing critical points. The measurement data can be stored as initial values for a subsequent simulation. Consequently, a method according to the invention facilitates a step in the direction of holistic lithography. This goal is known by the keyword "holistic litho" in the art.

Moreover, the exposure of an EUV mask with light in the EUV wavelength range facilitates an experimental examination of defect-free EUV masks. By way of example, it is possible to examine the exact placement of elements of the absorber structure. Therefore, a method according to the invention is suitable as a measurement tool for the further development of various types of EUV masks.

Finally, a method according to the invention is not restricted to the examination of EUV masks. Rather, it can also be used for analyzing mirrors for the EUV wavelength range.

Determining the behavior of the at least one element may comprise: determining a phase change and/or an amplitude change which is caused by the at least one element upon the irradiation with light in the EUV wavelength range.

For the purposes of analyzing the function of, for example, a phase-shifting element of a (future) EUV mask, it may be sufficient to analyze the phase change caused by the phase-shifting element. However, for analyzing critical points or defects, in particular defects of the multilayer structure, it is normally necessary to consider both the phase change and amplitude change of these elements. This will be explained below using the example of buried defects.

Buried defects are usually created at the substrate surface or by a local disturbance of the multilayer structure. These defects typically propagate through the multilayer structure. This results in a buried defect which yields both a reduced intensity or amplitude, the substantial parts of which are caused by a change in the surface inclination of the multilayer structure, and a modified phase front, which is predominantly caused by a change in the topography of the layers of the multilayer structure lying further down. The naturally arising defects of the multilayer structure consequently typically influence the amplitude and the phase of the light incident at the defect position, and hence also the light reflected by this point, at the same time. However, the weighting of the influence of buried defects on phase and amplitude varies significantly from defect to defect. Therefore, individually determining the phase error and the amplitude error of an examined defect is a precondition for the ideal repair of buried defects.

A method according to the invention does not indirectly gather the effect of buried defects of photolithographic masks at the actinic wavelength from measurements. Instead, a method according to the invention measures the defects at the actinic wavelength. As a result, the effects of the defects, as occur in a corresponding exposure apparatus, are examined in a direct manner. On the basis of these measurement data, amplitude and phase components are determined individually for each examined buried defect within the scope of a second step.

Examining the at least one defect may comprise a controlled modification of a phase of the light in the EUV wavelength range downstream of a reflection by the photolithographic mask.

Data or measurement data are obtained by virtue of the phase of the EUV radiation being modified in a defined manner over the defect and a plurality of measurements of the defect being carried out with a defined modified phase angle, the analysis of said data or measurement data allowing the ascertainment of both the phase component and the amplitude component of the examined defect.

The controlled modification of the phase of the light in the EUV wavelength range may comprise the introduction of a phase-shifting film into a beam path downstream of a reflection of the light in the EUV wavelength range by the photolithographic mask.

Introducing a phase-shifting film into the beam path may comprise: carrying out at least two measurements with phase-shifting films with different thicknesses.

Determining the amplitude and phase error may comprise: carrying out a recursive phase reconstruction algorithm with data from the at least two measurements.

In addition to a phase-shifting film with a varying thickness and a holding or displacement apparatus, this embodiment requires no additional components for the apparatus for examining defects on the EUV masks using light in the EUV wavelength range.

The measurement data of two or more measurements of the defect with a defined changed phase angle serve as input variables for carrying out a recursive phase reconstruction algorithm. By iterative propagation between the spatial domain and the frequency domain, it is possible to determine both the phase component and the amplitude component of the defect quantitatively from the data of two or more measurements of the defect. The basis for a best-possible repair concept of the examined defect is set by the quantitative amplitude and phase reconstruction of a defect on the basis of measurements at the actinic wavelength.

The material of the phase-shifting film may have a real part of refractive index <0.90, preferably <0.85, more preferably <0.80 and most preferably <0.75 in the EUV wavelength range. The film may comprise zirconium and/or the film may be arranged in a first pupil plane downstream of the photolithographic mask. The thickness of the film may vary in a range of 1 nm to 1000 nm, preferably 2 nm to 500 nm, more preferably 4 nm to 250 nm and most preferably 5 nm to 100 nm.

Examining the at least one defect may comprise the following steps: (a) carrying out at least two measurements of the defect at different incidence conditions of the light in the EUV wavelength range incident on the photolithographic mask; and (b) applying the recursive phase reconstruction algorithm to the data of the at least two measurements.

Additional information which is required to solve the phase problem by use of a recursive phase reconstruction algorithm is generated as a result of an overlapping measurement of the defect using EUV radiation at different angles. In addition to the phase of the buried defect reconstructed in this manner, it is also possible to reconstruct an image of the examined defect with an improved contrast. By comparing this image to the measured image of the defect, it is possible to make high-frequency image information visible, which disappears in the image noise and/or in the measured image.

Carrying out at least two measurements of the defect with different incidence conditions may comprise: carrying out at least two measurements of the defect at different angles using an at least partly coherent light source or inserting a monopole stop into the beam path upstream of the photolithographic mask and carrying out at least two measurements of the defect at different angles using an incoherent light source.

As a consequence, for the purposes of analyzing a buried defect of an EUV mask, it is possible to use both a coherent light source and an incoherent light source for the EUV wavelength range.

The monopole stop may comprise a sigma in the range of 0.01 to 0.6, preferably 0.02 to 0.5, more preferably 0.04 to 0.4 and most preferably 0.05 to 0.2. Here, sigma ($\sigma$) denotes a fraction of an aperture to the maximum aperture of the apparatus.

Currently preferred measurement systems employ incoherent light sources. As a rule, the necessary monopole stop is present in these metrology apparatuses. As a consequence, a unit for pivoting the monopole stop, and optionally the EUV beam incident on the stop, around the defect to be examined remains in terms of apparatus-based outlay.

The different angles of the at least two images may comprise an angular range of 0° to 25°, preferably 0° to 20°, more preferably 0° to 15° and most preferably 0° to 10°. The polar angle, i.e. the angle in respect of the perpendicular to the surface of the photolithographic mask, determines the angular range in which various imaging of a defect of an EUV mask is carried out.

Examining the at least one defect may comprise the following steps: (a) carrying out at least two measurements of the at least one defect with different focal positions, and (b) applying the recursive phase reconstruction algorithm to the data of the at least two measurements.

The input data for a recursive phase reconstruction algorithm are generated by virtue of measuring the optical intensities of at least two different but known focal positions of the EUV radiation, said input data sufficing for quantitatively ascertaining both the phase component and the amplitude component of the measured defect. This embodiment is advantageous as it requires no apparatus-based change of the measurement apparatus used for examining the defect of the photolithographic mask in the EUV wavelength range. Consequently, this embodiment only requires a subsequent calculation step.

The different focal positions may comprise a focal range of ±200 nm, preferably ±400 nm, more preferably ±800 nm and most preferably ±2000 nm in respect of a focal position on the surface of the photolithographic mask.

The at least two measurements may comprise a number of 2 to 500, preferably 3 to 200, more preferably 4 to 100 and most preferably 5 to 20 measurements.

The recursive phase reconstruction algorithm may comprise at least one algorithm from the group including: an iterative Fourier ptychographic algorithm, an inverse Fourier transform algorithm, a Gerchberg-Saxton algorithm, an error reduction algorithm, a gradient method and a hybrid input-output algorithm.

A criterion for the selection of the corresponding algorithm lies in the convergence behavior thereof for the respective input data.

The aspects of a defined method, described above with reference to a defect, may also be used to examine a critical point of a photolithographic mask for the EUV wavelength range.

As explained above, a method according to the invention allows the quantitative determination of the phase component and the amplitude component of a defect. Hence, the method according to the invention is able to analyze critical points. Critical points of the photolithographic mask are points whose parameters meet the specification but wherein at least one parameter of a critical point comes close to the corresponding defect threshold. The method according to the invention consequently renders it possible to measure each critical point on the mask, determine its phase and amplitude information and store this as an initial value for a subsequent simulation. Consequently, the method according to the invention facilitates a step in the direction of holistic lithography. As already mentioned above, this goal is known by the keyword "holistic litho" in the art.

The parameter value of the at least one critical point can reach ≥70%, preferably ≥80%, more preferably ≥90% and most preferably ≥95% of the defect threshold.

The method can furthermore include the steps of: (a) ascertaining a phase error and an amplitude error from the determined phase change and the determined amplitude change; and (b) ascertaining a repair concept for the at least one defect from the determined amplitude error and the determined phase error of the examined defect.

On the basis of the quantitative phase and amplitude components of the analyzed defects, it is possible to ascertain a best-possible repair concept for the examined defect.

According to a further aspect of the present invention, the above-described problem is solved by a method for compensating at least one defect of a photolithographic mask for an extreme ultraviolet (EUV) wavelength range. In an embodiment, the method includes the steps of: (a) analyzing data of the at least one defect; and (b) providing a phase-shifting structure on the photolithographic mask for compensating the examined defect.

As a result of the quantitative holistic analysis of the defects at the actinic wavelength, new perspectives emerge for the correction of defects, in particular for the compensation of buried defects of photolithographic masks in the EUV wavelength range. In particular, this renders it possible to follow repair approaches which go significantly beyond the compensating repair.

Analyzing data may comprise: analyzing a repair concept and/or ascertaining a repair concept from measurement data.

A method according to the invention for compensating a defect of an EUV mask can use data of an already existing repair form for the defect to be compensated. However, a method according to the invention can also be designed in such a way that a repair form for the defect to be corrected is produced from measurement data in a first step. Moreover, intermediate stages between these two poles are possible.

The provision of the phase-shifting structure may comprise: applying the phase-shifting structure on the examined defect for compensating the phase error of the examined defect.

The phase-shifting structure may comprise a layer of varying thickness of phase-shifting material which is applied onto the examined defect.

The provision of the phase-shifting structure may comprise: local removal of a layer of varying thickness over the examined defect.

In the case of specific defect types, it may be more expedient to compensate the defect by a local removal of material over the defect than to apply a phase-shifting structure of varying thickness over the examined defect. To this end, a changing thickness of the layer of material to be ablated over the defect is calculated. Which type of defect compensation is more advantageous for the considered defect is ascertained with the aid of the simulation, wherein the absorption of the phase-shifting structure of varying thickness is taken into account.

The precise defect analysis explained above facilitates the deposition of a phase-shifting structure onto the examined defect. The surface contour of a defect of a multilayer structure of an EUV mask can vary greatly. Thus, for example, defects in the form of a local bump can be extensive in the lateral direction or tend to be delimited locally. The height of a defect of the multilayer structure can range from zero or close to zero up to the two-digit nanometer range. By depositing phase-shifting material with a thickness that varies over the defect, it is possible, at least to a large part, to compensate the phase error of the examined defect.

The method for compensating the at least one defect may further include the step of: modifying at least one pattern element of the photolithographic mask for compensating an amplitude error of the examined defect.

The combined effect of the phase-shifting structure applied to the examined defect and of modifying at least one pattern element ensures that the region of the defect reflects the radiation incident at the actinic wavelength in the same way as a region of the multilayer structure which has no defect. The design of the phase-shifting structure takes account of the fact that the light in the EUV wavelength range is incident on the multilayer structure of an EUV mask at an angle (preferably 6° to 8°) in relation to the perpendicular. If some of a buried defect is covered by a pattern element of the absorber structure then this is also included in the calculation when designing the phase-shifting structure. Alternatively, or additionally, a part of one or more pattern elements can be modified in order to be able to repair the defect of the multilayer structure in an improved fashion. In particular, a part of one or more pattern elements can be removed.

By virtue of the repair of the examined defect removing the phase disturbance and intensity disturbance caused by the defect, the method described in this application facilitates a comprehensive compensation of buried defects. After the defect correction, the focal region that can be used by an exposure system has no noteworthy restrictions.

Modifying the at least one pattern element may comprise: removing a part of at least one pattern element which has the smallest distance from the examined defect.

Modifying the at least one pattern element for compensating the amplitude error may take account of an absorption of the light in the EUV wavelength range of the phase-shifting structure and/or of the phase-shifting layer of constant thickness.

For the purposes of compensating the phase portion of the examined defect, use is ideally made of a material which only shifts the phase of the actinic light without substantially absorbing the optical EUV radiation. Such materials are currently unknown. All currently known materials absorb a significant amount of EUV radiation in the EUV wavelength range. It is therefore advantageous to take into account the absorption caused by the phase-shifting structure and/or the phase-shifting layer of constant thickness in addition to the intensity disturbance caused by the defect when calculating the change in one or more pattern elements of the absorber structure.

Modifying at least one pattern element of the photolithographic mask for the extreme ultraviolet wavelength range may further include the step of: depositing at least a part of a pattern element for compensating the amplitude error of a examined defect.

The method for compensating at least one defect of a photolithographic mask for the extreme ultraviolet wavelength range may further include the step of: removing at least a part of at least one pattern element adjacent to the at least one defect by use of a second particle beam and an etching gas. The second particle beam may comprise an electron beam and the etching gas may comprise xenon difluoride ($XeF_2$).

The method for compensating at least one defect of a photolithographic mask for the extreme ultraviolet wavelength range may further include the step of: depositing at least a part of at least one pattern element by use of the second particle beam and a second deposition gas. The second deposition gas may comprise a metal carbonyl, such as chromium hexacarbonyl or dicobalt octacarbonyl.

As explained above, a repair process for the examined defect may comprise the removal of a part of a pattern element of the absorber structure. For the purposes of correcting an amplitude error of the examined defect, a subsequent application of a part of the partly removed pattern element or elements of the absorber structure may be expedient. In an alternative embodiment, compensating the at least one defect comprises simultaneous determination of a phase-shifting structure and a possibly necessary change in one or more pattern elements of the absorber structure.

The method further may include the step of: applying a phase-shifting layer of constant thickness in the region of the examined defect, wherein the thickness of the phase-shifting layer of constant thickness is selected such that a phase difference of the compensated defect in relation to a portion of the photolithographic mask without a defect is compensated.

As explained above, the combined effect of the phase-shifting structure applied to the defect and of the modification of at least one pattern element causes light at the actinic wavelength in the region of the defect to be reflected with the same phase front as from an undisturbed region of the EUV mask. However, the reflected phase front may have a constant phase difference relative to a phase front reflected from an undisturbed region of the EUV mask. The thickness of the phase-shifting layer of constant thickness is selected in such a way that the layer brings the phase angle of light from an undisturbed region and of light reflected from the region of the repaired defect into correspondence by way of a constant phase shift.

Modifying the at least one pattern element may take account of an absorption of the light in the EUV wavelength range of the phase-shifting structure and/or of the phase-shifting layer of constant thickness.

The phase-shifting structure and the phase-shifting layer of constant thickness may have the same material composition.

The provision of the phase-shifting structure and/or the phase-shifting layer of constant thickness may comprise: carrying out a deposition process by use of a particle beam and at least one precursor gas.

The material of the phase-shifting structure and/or the material of the phase-shifting layer of constant thickness may have a real part of a refractive index <0.90, preferably <0.85, more preferably <0.80 and most preferably <0.75 in the EUV wavelength range.

For the phase-shifting structure and/or for the layer of constant thickness, it is possible to select a material for which $\beta/\delta<1$, preferably <0.7, more preferably <0.5 and most preferably <0.3 applies at the actinic wavelength, where $\delta$ denotes the deviation of the real part of the complex refractive index from 1 and where $\beta$ denotes the imaginary part of the complex refractive index of the material of the phase-shifting structure and/or of the material of the layer of constant thickness.

From tables (such as e.g.: http://henke.lbl.gov.optical.constants/), it is possible to gather the optical properties of the various elements of the periodic system which come into question for providing a phase-shifting structure on a defect of a multilayer structure of an EUV mask and/or for providing a layer of constant thickness on the multilayer structure of an EUV mask.

The phase-shifting structure and the phase-shifting layer of constant thickness may have the same or a different material composition. This means that the phase-shifting structure and the phase-shifting layer of constant thickness may be deposited in a single process step.

The provision of the phase-shifting structure and/or the phase-shifting layer of constant thickness may comprise: carrying out a deposition process by use of a scanning particle beam and at least one precursor gas. The particle beam may comprise an electron beam, an ion beam, an atomic beam, a molecular beam and/or a photon beam. The precursor gas may comprise dicobalt octacarbonyl ($Co_2(CO)_8$), dirhenium decacarbonyl ($Re_2(CO)_{10}$), nickel tetracarbonyl ($Ni(CO)_4$) or tungsten hexacarbonyl ($W(CO)_6$).

The method for compensating the at least one defect may further include the step of: simulating the provision of a phase-shifting structure on the photolithographic mask and/or applying a phase-shifting structure of constant thickness in the region of the examined defect. Further, the method for compensating the at least one defect may include the step of: simulating the modification of the at least one pattern element which is adjacent to the at least one examined defect.

On the basis of the determined influence of amplitude and phase of the examined defect, it is possible to simulate the compensation of the phase error and/or of the amplitude error before carrying out the defect repair. As a result, the outlay for repairing the examined defect can be minimized. Moreover, the process window available for the repair can be ascertained with the aid of the simulation.

The method for compensating the at least one defect of a photolithographic mask for the extreme ultraviolet wavelength range may further include the step of: depositing the imaging structure on at least a part of the at least one defect by use of a first particle beam and a first deposition gas.

If the defect is not partly covered by the absorbing pattern element, it is preferable to apply the phase-shifting structure substantially centrally on the defect. However, if part of the defect of the multilayer structure is covered by a pattern element, the phase-shifting structure is designed in such a way that it corrects the non-covered and hence effective part of the buried defect.

Alternatively, the part of one or more pattern elements which covers the defect or defects of the multilayer structure may be removed prior to compensating the examined defect. This may initially be effectuated in the simulation prior to carrying out the repair process such that the effectuated repair process for the best-possible repair of the defect can be determined. Before attaching the ascertained repair form onto the defect, the part of the absorber pattern removed in the simulation is then in fact removed.

A computer program may comprise instructions which, when executed by a computer system, prompt the computer system to carry out the method steps of one of the above-described aspects.

In a further embodiment, an apparatus for examining at least one element of a photolithographic mask for an extreme ultraviolet (EUV) wavelength range comprises: (a) means for examining the at least one element with light in the EUV wavelength range; and (b) means for determining the behaviour of the at least one element upon irradiation with light in the EUV wavelength range.

The apparatus for examining the at least one element may be embodied to carry out the method steps of a first part of the above-described aspects.

The means for examining the at least one element may comprise an EUV-AIMS™ (Aerial Image Metrology System).

In yet another embodiment, an apparatus for compensating at least one defect of a photolithographic mask for an extreme ultraviolet (EUV) wavelength range comprises: (a) means for analyzing data of the at least one defect; and (b) means for providing a phase-shifting structure on the photolithographic mask for compensating the examined defect.

Finally, the apparatus for compensating the at least one defect may be embodied to carry out the method steps of a second part of the above-described aspects.

The details of one or more embodiments of the invention are set forth in the accompanying drawings and the description below. Other features, objects, and advantages of the invention will be apparent from the description and drawings, and from the claims.

DESCRIPTION OF DRAWINGS

The following detailed description describes currently preferred exemplary embodiments of the invention, with reference being made to the drawings, in which.

DETAILED DESCRIPTION

Currently preferred embodiments of the methods according to the invention and the apparatuses according to the invention are explained in greater detail below on the basis of the repair of multilayer defects of reflective photolithographic masks for the extreme ultraviolet (EUV) wavelength range (EUV mask). However, the methods according to the invention for examining and compensating defects of a photomask are not restricted to the examples discussed below. Instead, these can be used in the same way for repairing defects of various types of EUV masks, in particular, for example, for correcting phase-shifting EUV masks. Moreover, the methods according to the invention can be used, in general, for examining and compensating local defects of transmissive photolithographic masks.

Figure 1:
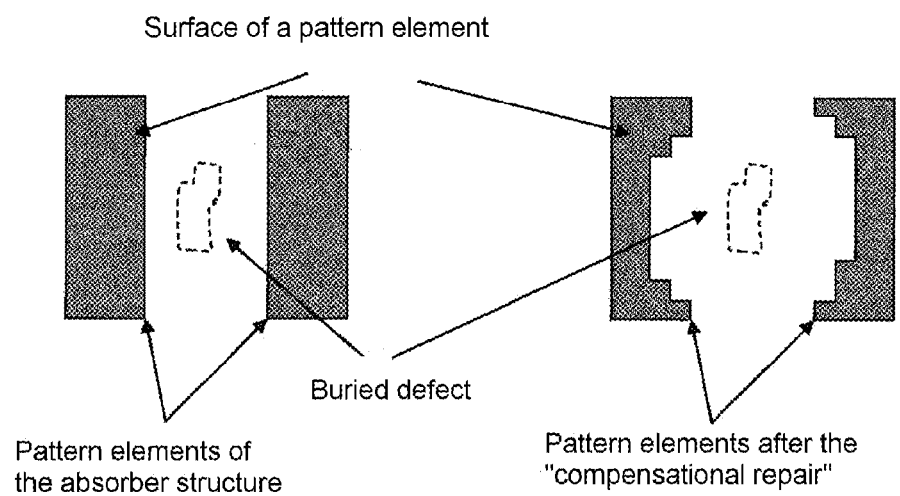
FIG. 1 schematically illustrates, in the left partial image, a plan view of a section of an EUV mask having a defect in a multilayer structure; and the right partial image reproduces the section of the left partial image after a compensational repair according to the prior art.

In the left partial image, FIG. 1 shows a plan view of a section of an absorbing EUV mask which is designed for an exposure wavelength in the region of 13.5 nm. The multilayer structure has a buried defect between the two pattern elements. The right partial image shows the section of the left partial image after carrying out a compensational repair by the removal of parts of both pattern elements, according to the prior art.

Figure 2:
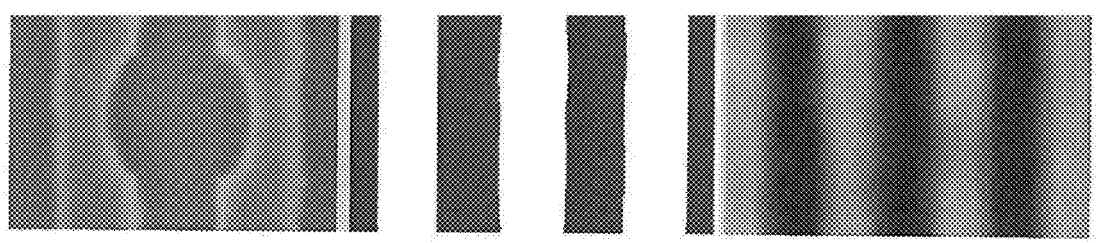
FIG. 2 schematically shows, in the left partial image, a plan view of a section of an EUV mask having a buried defect which was compensated by use of the compensational repair according to the prior art; the middle partial image illustrates a simulation of the image of the repaired mask region, wherein the focus of the radiation incident on the EUV mask has a maladjustment of −100 nm; and the right partial image presents an image of the mask section of the left partial image on a wafer, wherein the exposure system of the photolithography apparatus likewise has a focus maladjustment of −100 nm.

In the left partial image, FIG. 2 schematically presents a plan view of a section of an EUV mask having a buried defect which was repaired by use of the compensational repair according to the prior art. The middle partial image simulates the image of the repaired stripe structure of the left partial image on a wafer. In the simulation, the repaired region of the EUV mask has no disadvantageous effects on a wafer caused by the imaging behavior of the repaired region. However, the exposure system had a focus maladjustment of −100 nm. The right partial image presents an image of the stripe structure of the repaired region after an actually carried out exposure of a wafer. The exposure system of the photolithography apparatus had the same defocusing as in the simulation illustrated in the middle partial image.

The example of a compensational repair illustrated in FIG. 2 elucidates that the repaired defect requires a focus maladjustment of −100 nm so that the defect does not appear on a wafer. As a result, the usable working range of the lithography apparatus is drastically reduced if the corrected EUV mask can be used at all. Moreover, exposures outside of the focal plane in the EUV wavelength range are significantly more critical than at the position of the best focus since the dose distribution for achieving the specified CD (critical dimension) represents a critical parameter.

Figure 3:
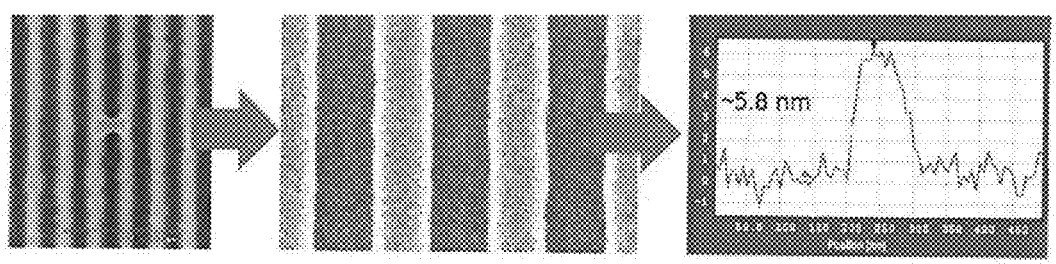
FIG. 3 shows, in the upper partial image sequence, the analysis of a buried defect using various metrology tools and reproduces, in the lower partial image sequence, the compensational correction according to the prior art of the identified buried defect and an image of the repaired region of the EUV mask on a wafer.
Figure 3:
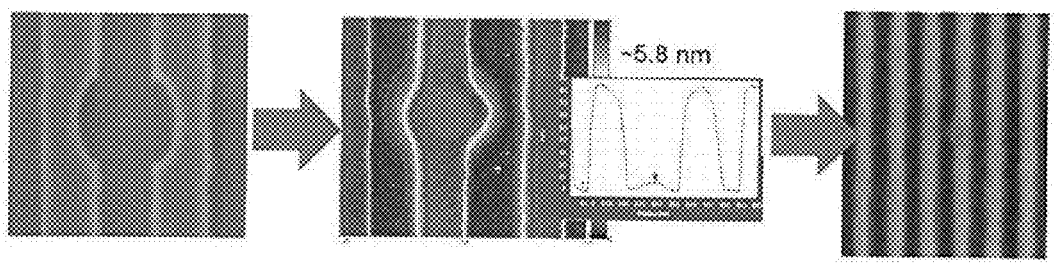

In the upper row of partial images, FIG. 3 shows the analysis of a buried defect of an EUV mask. The left upper partial image presents a defect which manifests itself when imaging the pattern elements on a wafer by way of an incorrect connection of two pattern elements which have the form of stripes. The buried defect is not visible when scanning the corresponding part of the EUV mask with an electron beam. The result of a scan of the electron beam is illustrated in the central upper partial image. The left upper partial image in FIG. 3 shows a scan of an atomic force microscope (AFM) over the defect. In the scan of the AFM, the buried defect appears in the form of a local bump with a height of approximately 5.8 nm. The lateral dimension of the buried defect in the scan direction is approximately 80 nm.

The lower row of partial images in FIG. 3 presents a compensational repair of the identified defect or an exposure of a wafer with the repaired region of the EUV mask, according to the prior art. The left lower partial image depicts the repaired region, as shown in an image of a scanning electron microscope (SEM). The central lower partial image shows a scan which was carried out over the repaired region using an AFM. The image insert of the central lower image, which presents an individual scan line of the AFM shows very clearly that the "compensational repair" leaves the buried defect untouched. In order to compensate the defect, a part of the absorbing material was removed from the pattern elements to the left and right of the identified defect. Finally, the right lower partial image reproduces the result of a wafer exposure of the repaired region of the EUV mask. The compensated defect is still visible on the wafer but no longer leads to a bridge connection of the two pattern elements adjacent to the defect.

Figure 4:
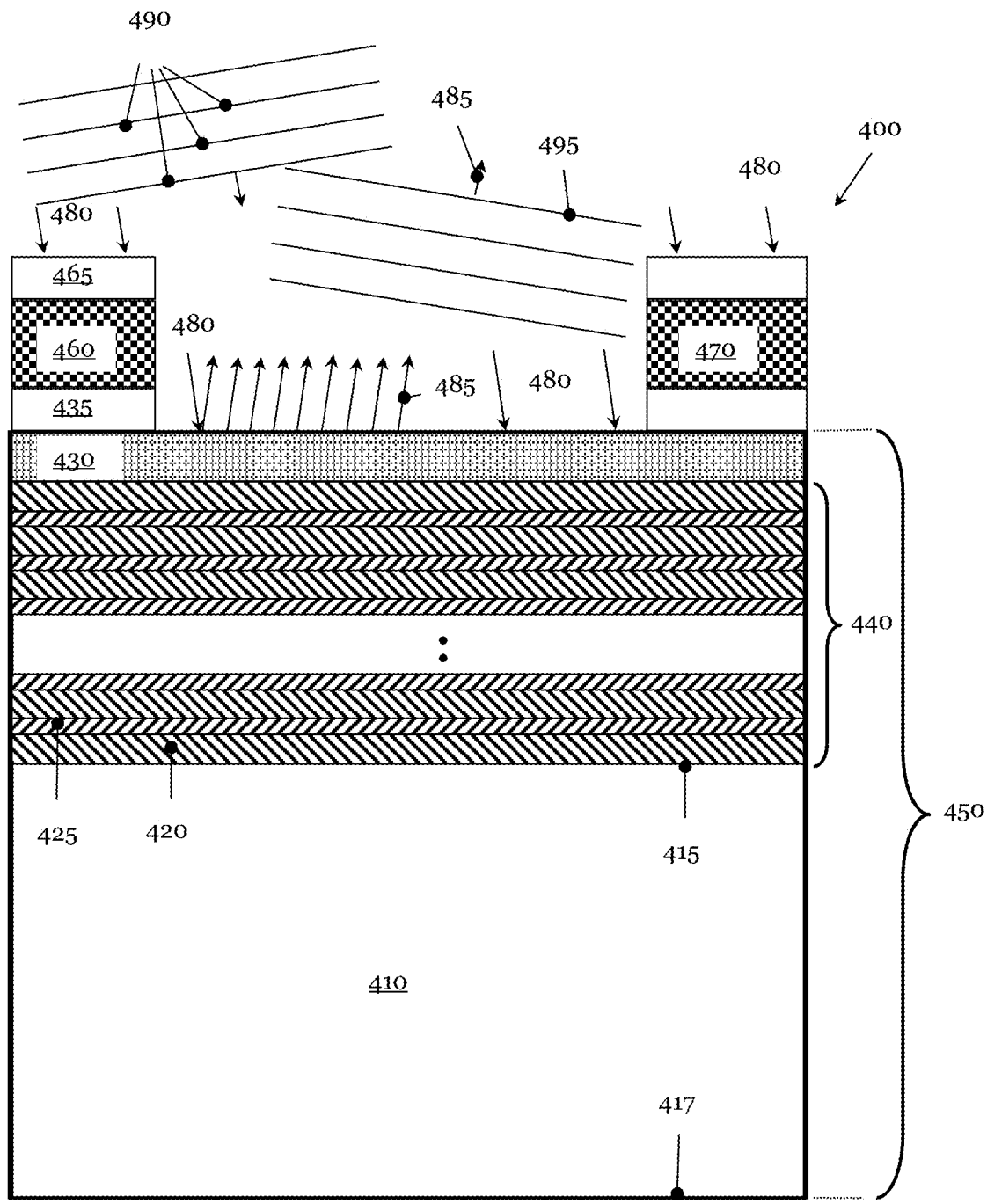
FIG. 4 schematically elucidates a cross section through an ideal photomask for the EUV wavelength range.

FIG. 4 shows a schematic section through a section of an absorbing EUV mask 400 for an exposure wavelength in the region of 13.5 nm. The EUV mask 400 has a substrate 410 made of a material with a low coefficient of thermal expansion, such as quartz, for example. Other dielectrics, glass materials or semiconducting materials likewise can be used as substrates for EUV masks, such as ZERODUIR®, ULE® or CLEARCERAM®, for instance. The rear side 417 of the substrate 410 of the EUV mask 400 serves to hold the substrate 410 during the production of the EUV mask 400 and during the operation thereof. A thin electrically conductive layer for holding the substrate 410 can be applied to the rear side 417 of the substrate 410 (not shown in FIG. 4).

A multilayer film or a multilayer structure 440 comprising 20 to 80 pairs of alternating molybdenum (Mo) 420 and silicon (Si) layers 425, which are also designated hereinafter as MoSi layers, is deposited onto the front side 415 of the substrate 410. The thickness of the Mo layers 420 is 4.15 nm and the Si layers 425 have a thickness of 2.80 nm. In order to protect the multilayer structure 440, a capping layer 430 made of silicon dioxide, for example, typically having a thickness of preferably 7 nm, is applied on the topmost silicon layer 425. Other materials such as ruthenium (Ru), for example, can likewise be used for forming a capping layer 430. Instead of molybdenum, it is also possible to use layers composed of other elements having a high mass number, such as e.g. cobalt (Co), nickel (Ni), tungsten (W), rhenium (Re), zirconium (Zn) or iridium (Ir), for the MoSi layers. The deposition of the multilayer structure 440 can be effectuated by ion beam deposition (IBD), for example.

The substrate 410, the multilayer structure 440 and the capping layer 430 are referred to hereinafter as mask blank 450. However, a structure having all the layers of an EUV mask, but without structuring of the whole-area absorber layer 460, may also be referred to as a mask blank 450.

In order to produce an EUV mask 400 from the mask blank 450, a buffer layer 435 is deposited on the capping layer 430. Possible buffer layer materials are quartz ($SiO_2$), silicon oxygen nitride (SiON), Ru, chromium (Cr) and/or chromium nitride (CrN). An absorption layer 460 is deposited on the buffer layer 435. Materials suitable for the absorption layer 460 are, inter alia, Cr, titanium nitride (TiN) and/or tantalum nitride (TaN). An antireflection layer 465, for example made of tantalum oxynitride (TaON), can be applied on the absorption layer 460.

The absorption layer 460 is structured, with the aid of an electron beam or a laser beam, for example, such that a structure of absorbing pattern elements 470 is produced from the whole-area absorption layer 460. The buffer layer 435 serves to protect a multilayer structure 440 when structuring the absorber layer 460, i.e. when producing the pattern elements 470.

The EUV photons 480 impinge on the EUV mask 400 with the phase front 490. The incident EUV photons 480 are absorbed in the regions of the pattern elements 470 and at least the plurality of the EUV photons 480 are reflected by the multilayer structure 440 in the regions which are free from absorbing pattern elements 470. The phase front 495 symbolizes the outgoing electromagnetic wave 485 reflected by the multilayer structure 440.

The multilayer structure 440 should be designed in such a way that the layer thicknesses of e.g. a molybdenum layer and a silicon layer correspond to an optical thickness of $\lambda/2$ of the actinic wavelength for the EUV photons 480 that are incident on the multilayer structure 440 at the predetermined angle of incidence. A deviation from this condition leads to a local violation of Bragg's reflection condition and hence to a change of the locally reflected light in the EUV wavelength range. On account of the very small wavelengths, the EUV range places extreme requirements on the homogeneity of the individual layers of the multilayer structure 440 and on their surface roughness over the area of the EUV mask 400. Therefore, there may be deviations in the real layer thicknesses of individual layers from a predetermined layer thickness during the production process of the multilayer structure 440—as already mentioned above. Further, a small local unevenness of the substrate 410 of the EUV mask 400 can propagate through the multilayer structure 440.

Figure 5:
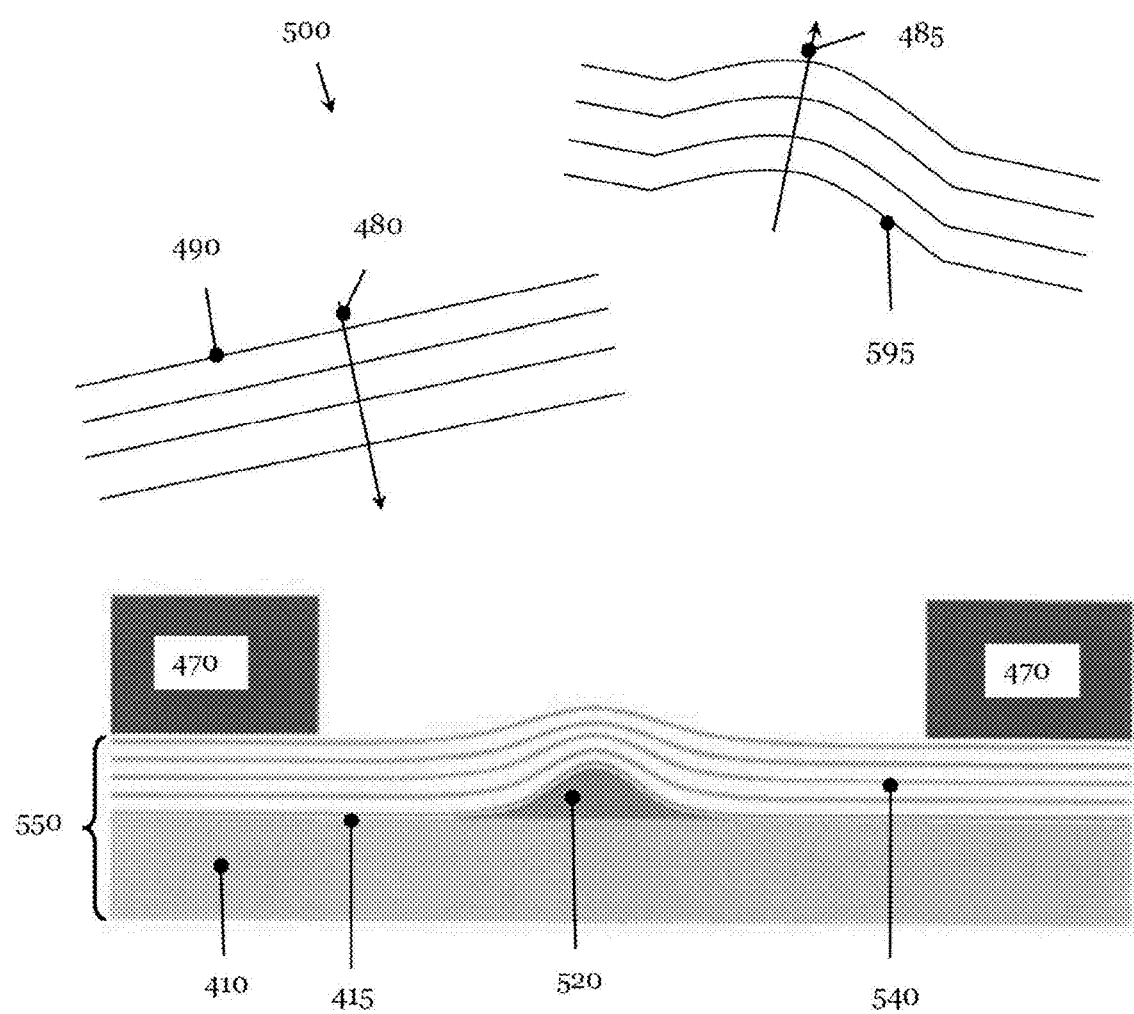
FIG. 5 schematically reproduces a cross section through a region of a photomask for the EUV wavelength range (EUV mask), which has a buried defect localized on the surface of the substrate, on which the multilayer structure is applied to the substrate.

FIG. 4 illustrates an ideal EUV mask 400. The EUV mask 500 of FIG. 5 shows a section through a region of the mask 500 having a buried defect 520, which is located on the surface of the substrate 410, on which the multilayer structure 540 of the EUV mask 500 is arranged. The buried defect 520 results in a disturbed multilayer structure 540 in the region of the defect 520. The defect 520 leads, firstly, to EUV radiation being scattered from the direction of the reflected beam 485 in the region of the defect. As a result, less EUV radiation is reflected in the direction of the reflected beam from the region of the EUV mask 500 having the buried defect 520. Secondly, the layer thicknesses of the MoSi layers of the multilayer structure 540 which are disturbed in the region of the defect 520 lead to disturbance in the phase of the light in the EUV wavelength range reflected from the region of the defect 520. This is elucidated in the example of FIG. 5 by the disturbed phase front 595.

The buried defect 520 illustrated in an exemplary manner in FIG. 5 has the form of a local bump. Tiny scratches may arise during the polishing of the surface 415 of the substrate 410 (not illustrated in FIG. 5). As already discussed in the introductory part, during the deposition of the multilayer structure 540, particles on the surface 415 of the substrate 410 may be overgrown or particles may be incorporated into the multilayer structure 540 (likewise not shown in FIG. 5).

The buried defects 520 of an EUV mask 500 may have their starting point in the substrate 410, on the front side or the surface 415 of the substrate 410, in the multilayer structure 540 and/or on the surface 560 of the mask blank 550 (not shown in FIG. 5). Defects 520 that are existent on the front side 415 of the substrate 410 may change both their lateral dimensions and their height during the propagation in the multilayer structure 540. This may occur in both directions, i.e. a defect 520 may grow or shrink in the multilayer structure 540 and/or may change its form. Buried defects 520 of an EUV mask 500 which do not originate exclusively on the surface 460 of the capping layer 430 are referred to as buried defects in this application—as already explained above.

As likewise already mentioned above, various defect types may be present in a mask blank or on an EUV mask 500. The various types of buried defects 520 can be examined and compensated using all methods described below.

Figure 6:
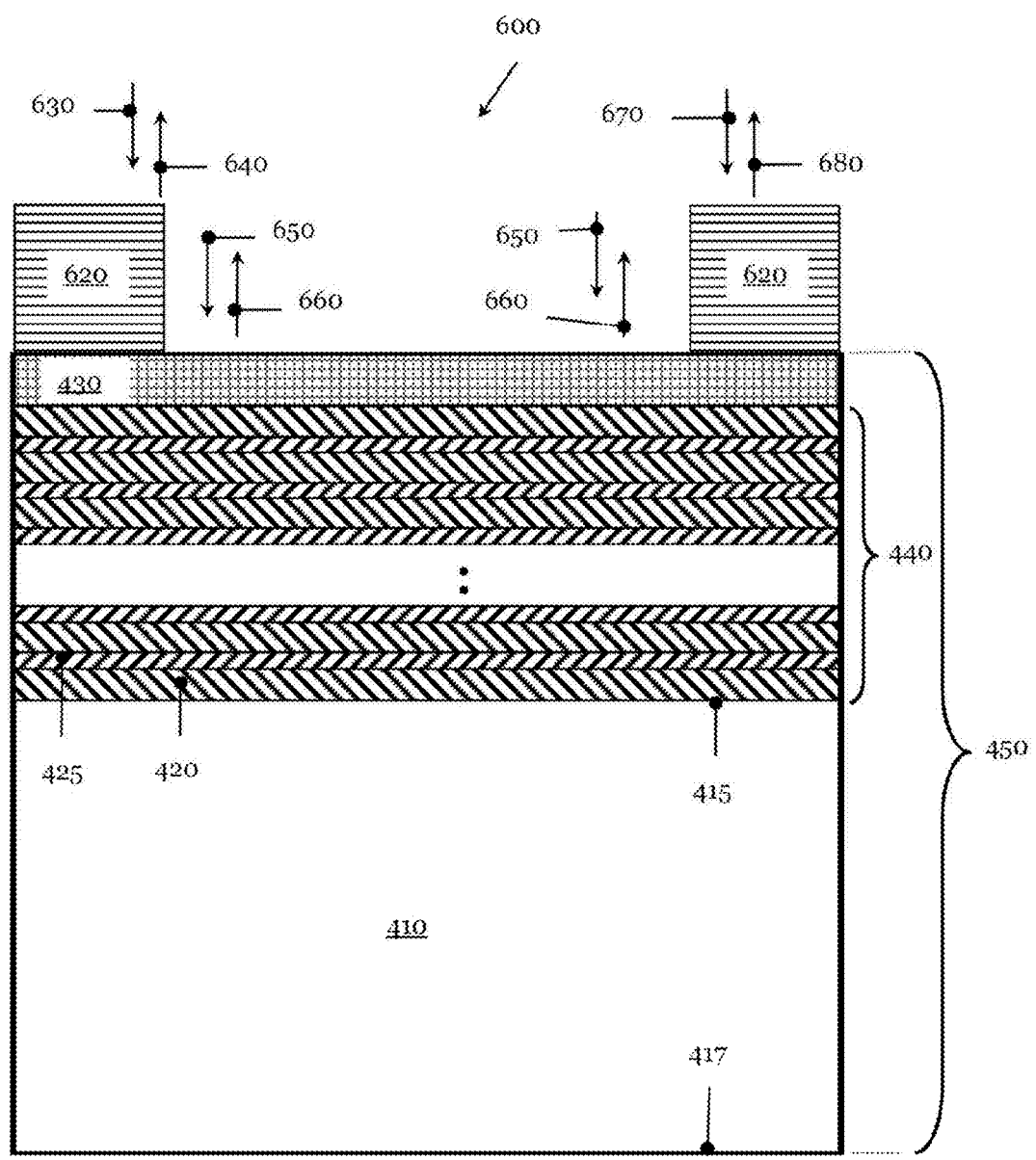
FIG. 6 schematically illustrates a cross section through a phase-shifting EUV mask.

The defect 520 in FIG. 5 represents a first example of an element of an EUV mask which can be examined using a method described in the "Summary" section. FIG. 6 presents a second example of an element of an EUV mask 600 which can be analyzed with the aid of incident EUV radiation. The EUV mask 600 in FIG. 6 shows the substrate and the multilayer structure 440 of FIG. 4 or of the mask blank 450 of FIG. 4. In place of a pattern made of absorbing pattern elements 470 of FIG. 4, the EUV mask 600 in FIG. 6 has a pattern of phase-shifting pattern elements 620. The height of the phase-shifting pattern elements 620 is determined with the aid of EUV radiation incident 650 on, and reflected 660 by, the mask blank in comparison with EUV radiation 640, 680 incident 630, 670 on, and reflected by, the phase-shifting pattern elements 620. The height of the phase-shifting pattern elements 620 can be calculated from the phase difference of the reflected 640, 660 or 640, 680 EUV radiation. Here, the assumption is made that the material composition of the phase-shifting pattern elements 620 is known. If the latter is not known, it likewise can be ascertained from an analysis of the amplitude change of the radiation reflected by the mask blank 450 and the pattern elements 620. Moreover, in addition to the height of the phase-shifting pattern elements 620, it is also possible to determine the position thereof on the multilayer structure 540.

Figure 7:
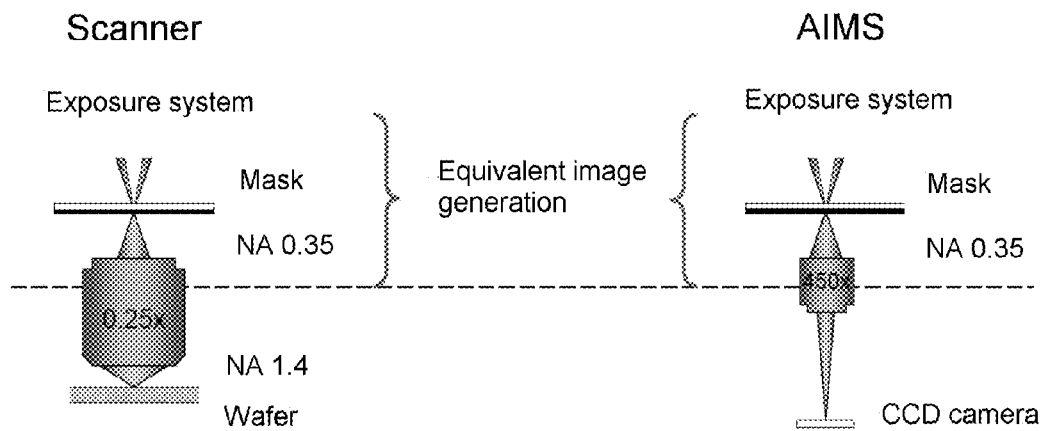
FIG. 7 schematically elucidates the principle of an AIMS™ in comparison with a scanner.

FIG. 7 elucidates the principle of an AIMS™ (Aerial Image Metrology System). Some components of a scanner are illustrated schematically in the left partial image. An exposure system focuses electromagnetic radiation of the actinic wavelength onto a photolithographic mask. A projection optical unit images the radiation passing through the photomask with reduction (typically 1:4 or 1:5) on a wafer or on a photoresist distributed on the wafer with a large numerical aperture (NA). The right partial image shows a few components of an AIMS™ for the same actinic wavelength of the scanner of the left partial image. The exposure system of the scanner and of an AIMS™ are substantially identical. This means that the image production is substantially the same for both systems. Consequently, the AIMS™ images a mask how the latter in fact sees a wafer. However, unlike in the case of a scanner, a lens images a small section of a photomask with great magnification on a CCD (charge-coupled device) camera in the case of an AIMS™. As a result, it becomes possible to illustrate defects which the photomask has at the actinic wavelength in its aerial image and detect said defects with the aid of a CCD sensor or a CCD camera. FIG. 7 shows an AIMS™, which is used to analyze transmissive photomasks.

Figure 8:
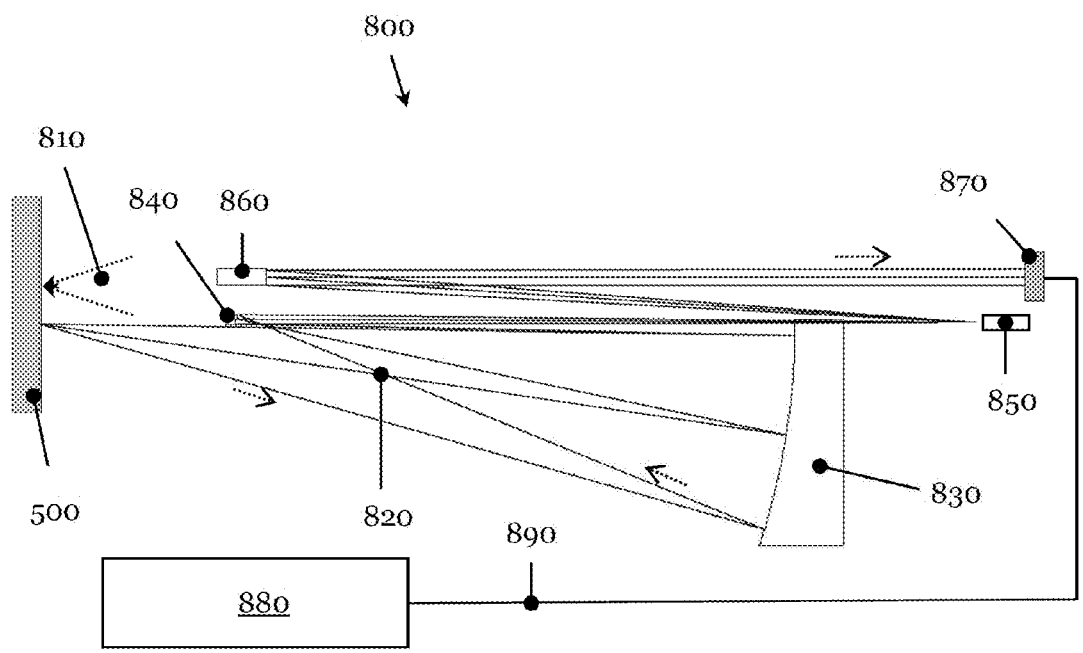
FIG. 8 schematically presents a detection system of an AIMS™ for the EUV wavelength range (EUV-AIMS™)

FIG. 8 schematically shows an example of an optical detection system 800 of an AIMS™ for the EUV wavelength range. As already mentioned previously, only reflective components are currently used in photolithography systems for the EUV wavelength range. For reasons of clarity, the exposure system of the AIMS™ for the EUV wavelength range, abbreviated EUV-AIMS™, is suppressed. On the EUV mask 500, which has an element with a buried defect 520, light in the EUV wavelength range, which has a wavelength of, for example, 13.5 nm, is focused on the structured side of the EUV mask 500. Typically, the radiation 810 incident on the EUV mask, and hence also the EUV radiation reflected by the multilayer structure 540, includes an angle of 6° to 9° with respect to the perpendicular to the mask. This is likewise suppressed in the schematic illustration of FIG. 8. The radiation 820 reflected by the EUV mask is collected by the first mirror 830 of the detection system 800 and transmitted to the second mirror 840. The radiation 820 reflected by the EUV mask 500 is directed to the CCD camera 870, which detects the EUV radiation, via a third mirror 850 and a fourth mirror 860. In the example illustrated in FIG. 8, the first mirror 830 is an aspherical mirror and the mirrors 840, 850 and 860 have a spherical form. The distance between the EUV mask 500 and the CCD camera 870 is of the order of one meter.

The exemplary detection system 800 in FIG. 8 further has an analysis unit 880 which is connected to the CCD sensor 870 by the connection 890. The analysis unit 880 receives measurement data from the CCD sensor 870 and it is designed to control the CCD sensor. Further, the analysis unit 880 can analyze the received measurement data and ascertain a repair concept for the defect 520 of the EUV mask 500.

Data or measurement data of more than one image of the defect 520 are necessary in order to be able to quantitatively determine the error in the reflected phase front (phase error) caused by the defect 520 of the EUV mask 500 and the deviation of the intensity (amplitude error) reflected from the region of the buried defect 520. At least three different methods can be used to produce the data or measurement data which allow ascertainment of both the phase error and the amplitude error of the identified buried defect 520.

In a first option, it is possible to record a series of wafer exposures and/or a number of aerial images. Here, the focal plane of the exposure system is systematically modified from above the EUV mask to below the EUV mask 500. The upper partial image in FIG. 9 elucidates this relationship. If the focal plane of the exposure system lies above the mask, this is referred to as positive ("+") defocusing or overfocusing. In the upper partial image of FIG. 9, this case is symbolized by dotted lines. By contrast, if the focal plane of the exposure system lies in the mask itself, as illustrated in an exemplary manner by dashed lines in the upper partial image of FIG. 9, this is referred to as negative ("−") defocusing or underfocusing.

Figure 9:
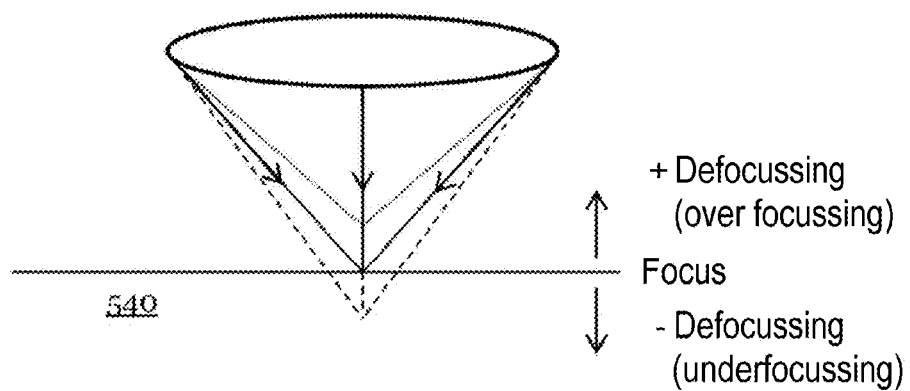
FIG. 9 defines the defocusing in the upper partial image and, in the lower partial image, schematically presents the intensity profile on a wafer or a CCD camera of an EUV-AIMS™ during a number of measurements through the focus from FIG. 5.
Figure 9:
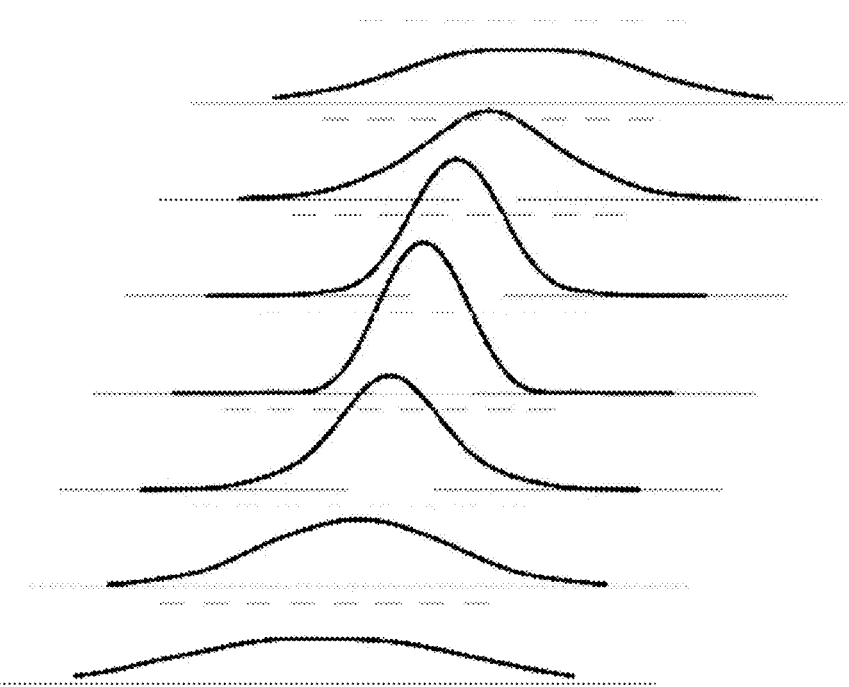

The lower partial image of FIG. 9 elucidates the optical intensity distribution of a series of aerial images or of wafer exposures during the measurement through the focus. For the purposes of determining the phase error and the amplitude error caused by the buried defect 520 as accurately as possible, it is expedient to record a large number of recordings or images of the region of the buried defect 520 when tuning the focus or the focal plane from underfocusing to overfocusing. The suitable number depends on the defect type to be analyzed. With the exception of specific defects, 10 to 100 images are typical. Tuning of the focal plane can be effectuated by changing the focusing of the exposure device of the EUV-AIMS™ or, in the case of stationary focus, by displacing the EUV mask 500 in the direction of the EUV beam.

A phase reconstruction algorithm is effectuated with the produced data as input data in order to determine the phase error and the amplitude error of the buried defect 520. For the first option of the measurement data generation, discussed here, use can be made, for example, of the Gerchberg-Saxton algorithm or the IFTA (Inverse Fourier Transform Algorithm) as phase reconstruction algorithm.

This first option for ascertaining data or measurement data as input for a phase reconstruction algorithm has the great advantage that there is no need to modify an EUV-AIMS™ in order to generate the input data for the phase reconstruction algorithm.

Figure 10:
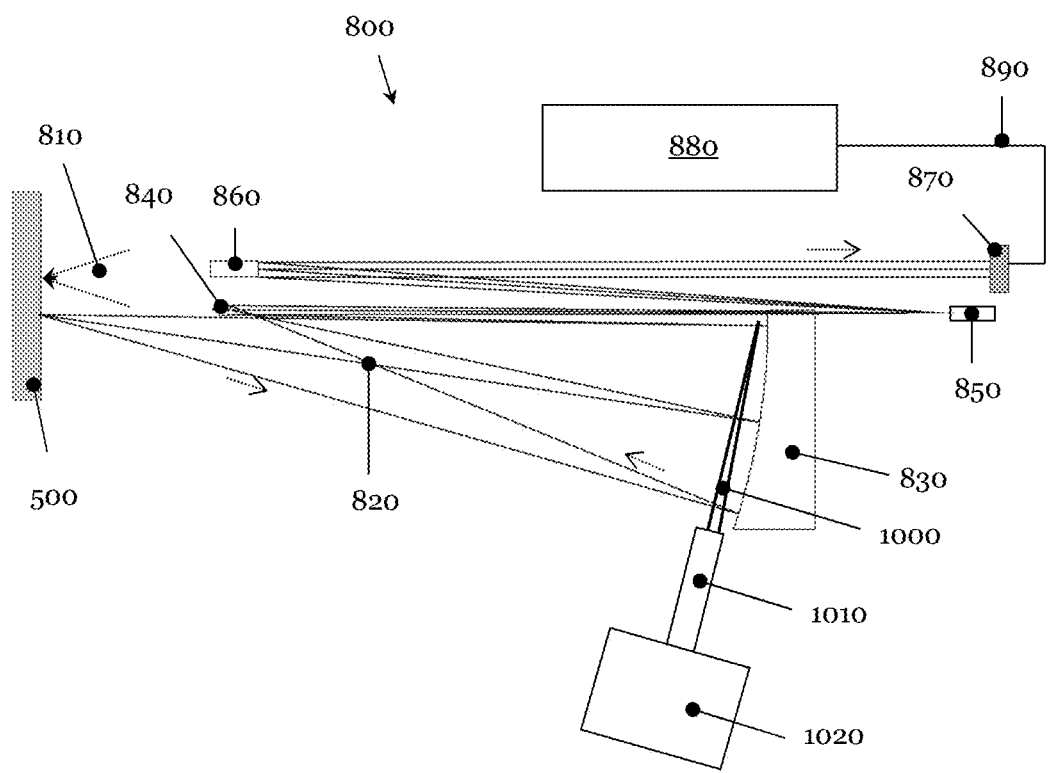
FIG. 10 repeats the detection system of FIG. 8, into which, additionally, a phase-shifting film has been introduced upstream of the first mirror.

FIG. 10 schematically illustrates a second option for recording a series of aerial images of the buried defect 520. FIG. 10 once again shows the optical detection system 800 of the EUV-AIMS™ of FIG. 8. Upstream of the first mirror 830 of the detection system 800, a phase-shifting film 1000 has been introduced into the beam path of the light for the EUV wavelength range that has been reflected by the EUV mask 500. The thickness, and hence also the optical thickness, of the phase-shifting film 1000 varies in a defined manner in the film plane and hence perpendicular to the EUV light incident on the mirror 830. The phase-shifting film 1000 is applied to a movement apparatus 1020 by way of a holder 1010. The movement apparatus 1020 can drive the phase-shifting film 1000 in a defined manner into and out of the beam path of the radiation 820 reflected by the EUV mask. As a result, it is possible to effectuate a plurality of images of the buried defect 520 with defined wavefront modifications. The data produced thus may, in turn, be used as input data for carrying out a phase reconstruction algorithm.

In order to determine the phase error and the amplitude error of a buried defect, the images can be analyzed with a defined angle change by use of an error reduction algorithm or gradient method.

Similar to the first option, which was explained in the context of FIG. 9, it is also advantageous to generate a large number of images of the buried defect 520 with a large span width of modified wavefronts for the second option of input data generation for the analysis with a defined angle change. As a result, a quantitative determination of the phase error and amplitude error of the buried defect 520, which is as precise as possible, is facilitated. For defects 520 which have not dropped out, 5 to 50 images with various positions of the phase-shifting film 1000 in the beam path of the reflected radiation 820 are required in normal circumstances. For the phase-shifting film 1000, it is expedient to select a material which, in a defined manner, modifies the phase of the EUV radiation reflected by the mask 500 and, at the same time, absorbs EUV radiation to the smallest possible extent. This is achieved by materials whose k-value is as small as possible. In the variable k=β/δ, β describes the imaginary part of the complex refractive index and δ denotes the deviation of the real part of the complex refractive number from 1 (n=n−iβ=1−δ−iβ). Examples of materials which have a relatively large deviation of the real part of the complex refractive index from 1 are the following metals that were already mentioned in the context of FIG. 4: molybdenum (Mo), cobalt (Co), nickel (Ni), tungsten (W), rhenium (Re), zirconium (Zr) or iridium (Ir).

The varying thickness of the phase-shifting film 1000 preferably comprises a range from 1 nm (at the thin end) to 100 nm (at the thick end). The thickness of the phase-shifting film can vary continuously in the film plane, as illustrated schematically in FIG. 10. It is also possible that the phase-shifting film 1000 has a stepped thickness. Further, it is possible to use two or more films with a constant thickness. The phase-shifting effect then is adjusted by the arrangement thereof in the beam path of the EUV radiation 820. When designing the thickness of the phase-shifting film 1000, it should be noted that the EUV radiation passes through the film twice. Currently, a Zr-film is preferably used as a phase-shifting film 1000.

Figure 11:
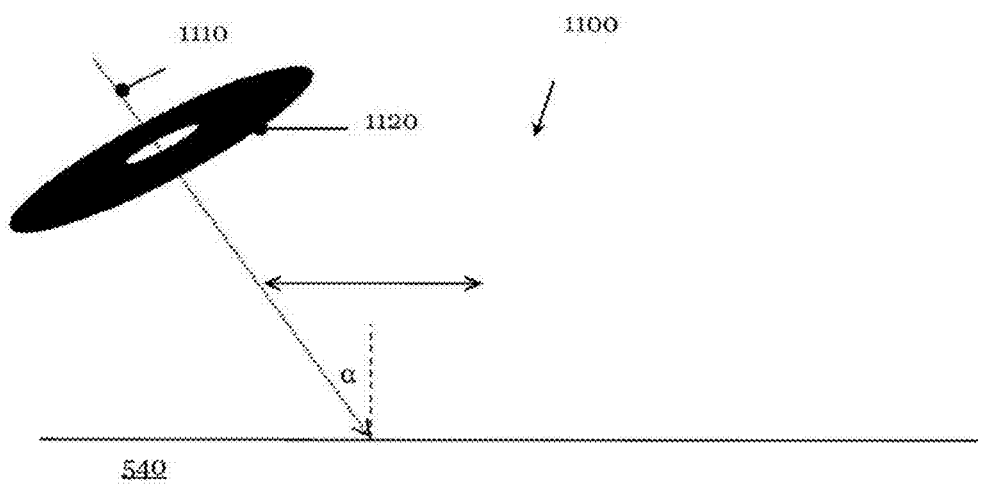
FIG. 11 schematically illustrates scanning in an angular range of 2·α over a defect of an EUV mask, wherein, a monopole stop, which is moved synchronously with the EUV beam over the angular range of 2·α, is applied at the output of the exposure system of the EUV-AIMS™.

The diagram 1100 in FIG. 11 illustrates a third option for generating measurement data which can be used as input data for carrying out a phase reconstruction algorithm. A pinhole 1120 or a monopole stop 1120 is inserted into the EUV beam 1110 that leaves the exposure system of the EUV-AIMS™. By way of example, the monopole stop 1120 can have a sigma of 0.1, i.e. the monopole stop 1120 has an aperture or an opening which corresponds to 10% of the diameter of the beam at the output of the exposure system of the EUV-AIMS™. The pinhole 1120 acts as a point light source for the EUV radiation 1110. The region of the multilayer structure 540 having the buried defect 520 is scanned at various angles α. Here, α denotes the polar angle of the photolithographic mask 500, i.e. an angle related to the perpendicular to the mask plane. The angular range over which measurements are undertaken comprises 2·α. As a result, images of the defect 520 are generated at different observation angles. These measurement data serve as input data for carrying out a phase reconstruction algorithm for ascertaining the phase error and the amplitude error of the buried defect 520.

For the third option of the measurement data production, discussed here, use can be made of, for example, a Fourier ptychographic algorithm as a phase reconstruction algorithm.

The variation of the angle α typically lies in the range of ±15° about the perpendicular to the surface of the EUV mask 500. The number of measurements to be carried out in this angular range preferably lies in the range of 5 to 50 measurements.

In order to be able to expose the buried defect 520 at different angles, the exposure system of the EUV-AIMS™ must have a beam tilting apparatus which, together with the pinhole 1120, allows the EUV beam 1010, which exposes the mask 500, to be modified over a defined angular range about an axis perpendicular to the mask 500 (not shown in FIG. 11). A beam tilting apparatus can be realized by tilting or rotating one or more mirrors of the exposure system in combination with, parallel therewith, tracking of the monopole stop 1120.

In an alternative embodiment, the EUV beam is not moved around the buried defect 520 but the EUV mask 500 is moved relative to the EUV beam (not illustrated in FIG. 11). To this end, the holding apparatus of the EUV mask 500 can be equipped with an appropriate movement apparatus.

The exemplary EUV-AIMS™ of FIG. 11 has an EUV radiation source which produces incoherent radiation. If an EUV-AIMS™ has a coherent EUV radiation source, it is possible to dispense with the installation of a pinhole 1120 into the EUV-AIMS™ for the purposes of scanning the buried defect 520 over a predetermined angular range.

The multilayer structures 440, 540 of current EUV masks 400, 500 are typically optimized for a maximum reflection at 6° in the direction of the normal. In current EUV-AIMS™, illumination angles emerging from NA cones that are inclined by 6° are possible, the latter corresponding to an angular range from approximately 10° to 2° with respect to the normal. A relative tilt between incident EUV radiation and the normal of the EUV mask within an angular range of ±15° about the perpendicular to the surface does not violate Bragg's reflection condition significantly.

Figure 12:
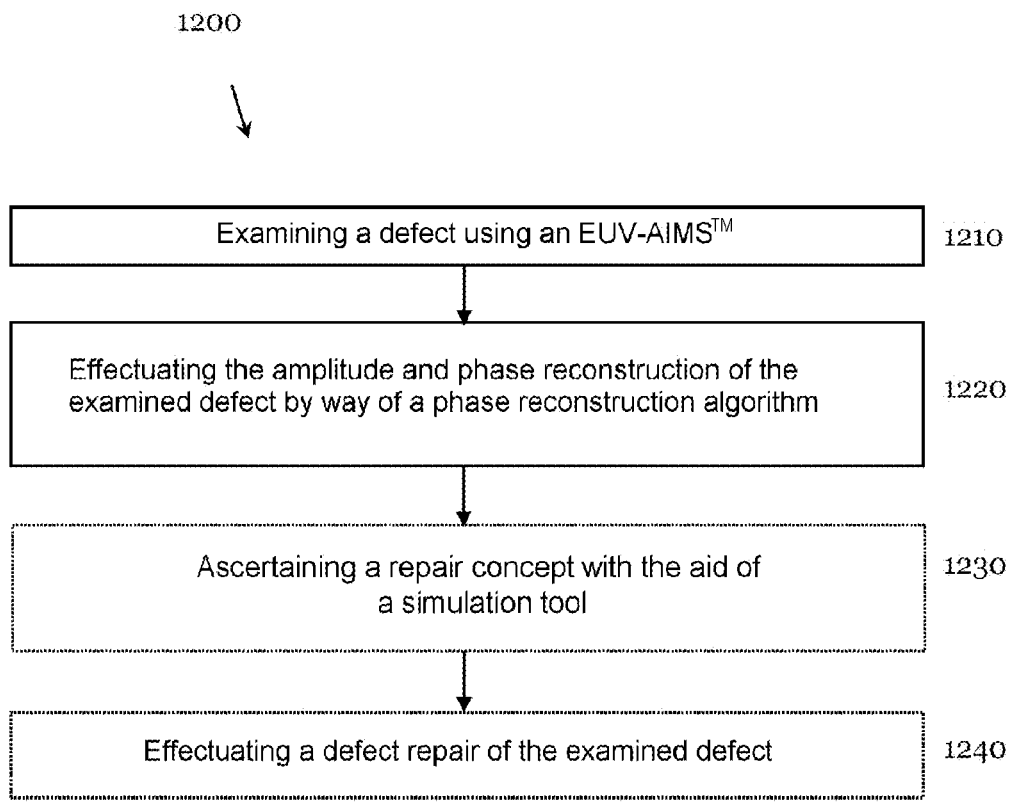
FIG. 12 schematically presents an overview of various steps of a defect analysis and of a defect repair.

The flowchart 1200 in FIG. 12 provides an overview over the processes of the methods for examining a defect 520 of an EUV mask 500 at the actinic wavelength and for correcting the examined defect 520. An identified defect 520 is examined with the aid of an EUV-AIMS™ in the first step 1210. Three different measurement methods were explained above in relation to this step. In the second step 1220, there is an amplitude and phase reconstruction of the examined defect 520. To this end, a phase reconstruction algorithm is carried out using the measurement data produced in the first step as input data. Respective algorithms allowing the determination of the phase error and the amplitude error from the generated measurement data were specified within the scope of the discussion of the various measurement methods.

A repair concept is ascertained for the examined defect 520 in the third step 1230 with the aid of the simulation. This is carried out on the basis of the quantitative phase and amplitude errors determined in the second step. The following diagram 1300 in FIG. 13 outlines an example of ascertaining a repair form. This step does not lie in the focus of the present application and it is therefore only discussed briefly.

Finally, the examined defect 520 is repaired in the fourth step 1240 on the basis of the best-possible repair concept ascertained in the third step. This step is explained in more detail below.

Figure 13:
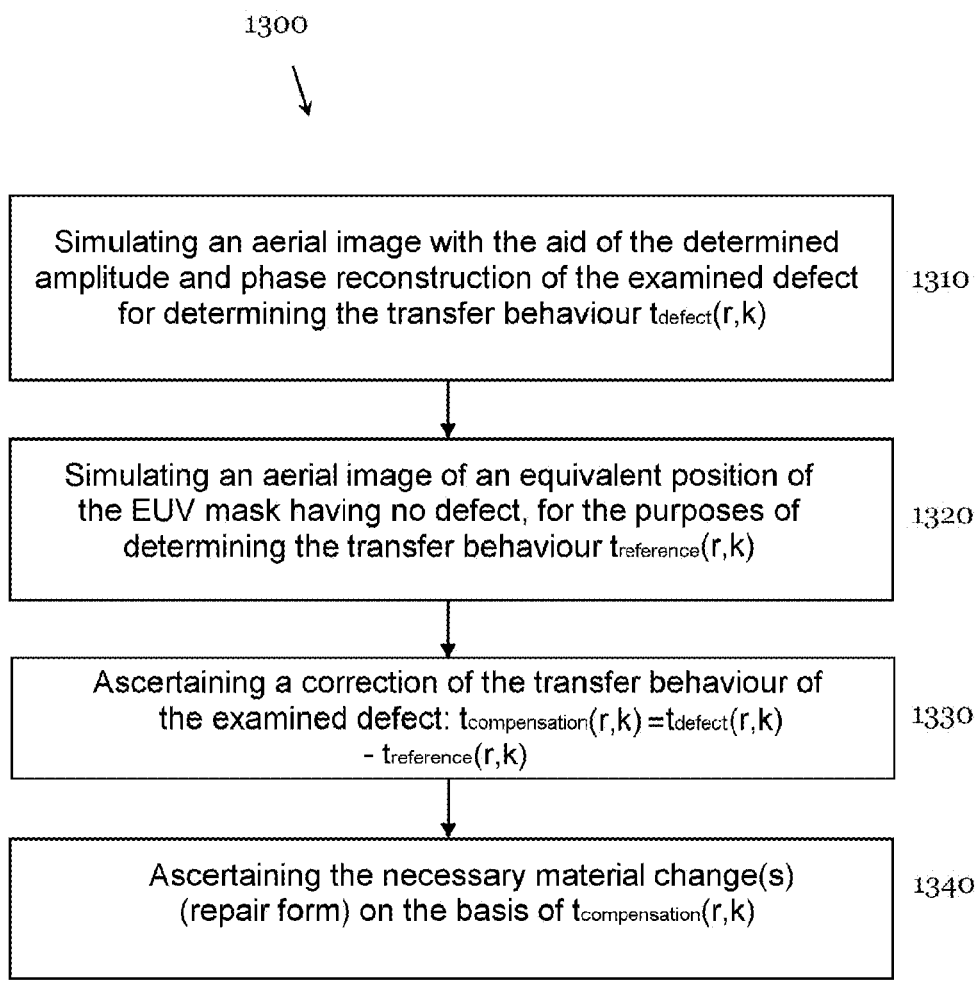
FIG. 13 indicates an overview of the four steps for producing a repair form.

The diagram 1300 in FIG. 13 elucidates the four steps for determining a repair concept. An aerial image of the examined defect 520 is simulated in the first step 1310. The simulation is carried out on the basis of the amplitude and phase change caused by the defect 520. This in turn is based on measurement data supplied by an EUV-AIMS™. As a result, the transfer method of the defect 520 is determined as a function of location and frequency or wave number $k(t_{defect}(r,k))$. For the EUV-AIMS™ measurements, use can be made of the illumination setting of a corresponding wafer exposure apparatus; this is referred to as "scanner matching" in technical jargon. In an alternative embodiment, work can be carried out with an exposure setting which is optimized for a maximum measurement accuracy of the repair concept. By way of example, the phase effects of buried defects 520 are particularly dominant under coherent illumination and therefore measurable in a particularly accurate manner under these conditions.

Thereupon, an equivalent point of the EUV mask 500 which does not have a defect is simulated in the second step 1320. As a result of this, a reference transfer behavior $(t_{reference}(r,k))$ of the EUV mask 520 for the position of the defect is ascertained. The simulation of a reference position can be effectuated on the basis of measurement data of a defect-free equivalent position, which are likewise determined with the aid of an EUV-AIMS™, and/or with the aid of design data of the EUV mask 500 ("die to database"). An equivalent position is a point on the EUV mask 500 which is surrounded by the same arrangement of pattern elements as the defect-afflicted point.

In the third step 1330, the extent of the correction of the transfer behavior ($t_{compensation}(r,k)$) is determined such that the defect 520 substantially has the same transfer behavior (i.e. reflection behavior) as a reference position.

Finally, the material change(s) which is (are) required to obtain the intended transfer behavior of the defect 520 are calculated in the fourth step 1340. The material change may comprise the application of material on and the removal of material from the defect 520. Further, the change in material may comprise the removal and the deposition of parts of absorbing and/or phase-shifting pattern elements. The material change(s) for the material involved in the repair process (or for all materials involved in the repair process) are optimized on the basis of material constants and the properties of the repair process, and a repair concept is created thereby. An EUV-AIMS™ can be used to calibrate the material properties of the material (or materials) involved in the repair process. Details in this respect are explained in the context of the discussion of the following figures. Consequently, the repair concept describes the material change(s) to be carried out in the region of the defect 520 for the purposes of compensating the amplitude and phase change caused by the buried defect.

Figure 14:
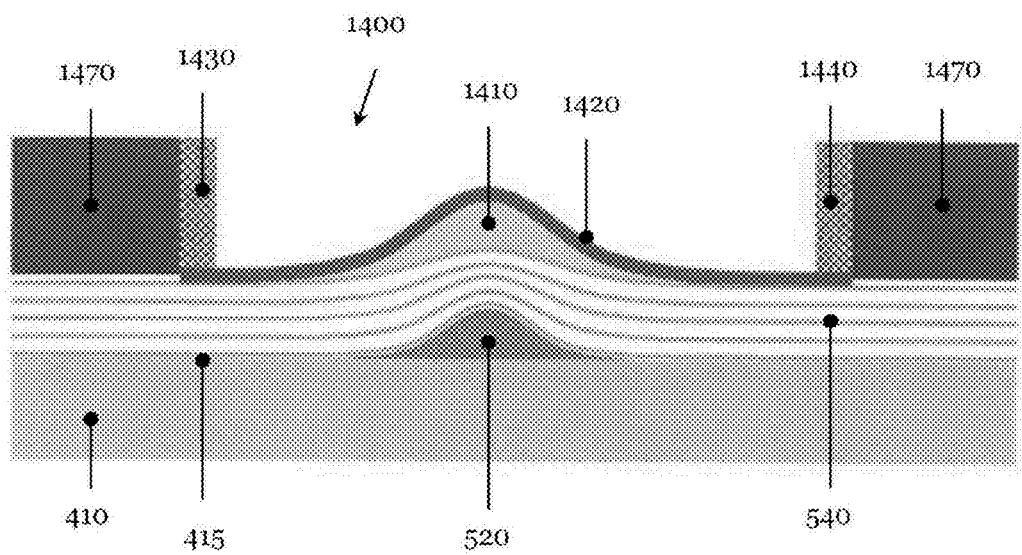
FIG. 14 illustrates FIG. 5 after repairing the phase error and the amplitude error of the buried defect, wherein a phase-shifting layer of constant thickness additionally corrects a constant phase difference in relation to the reflection from an undisturbed region of the EUV mask.

The diagram 1400 in FIG. 14 shows the EUV mask 500 of FIG. 5 after the buried defect 520 has been repaired. A phase-shifting structure 1410 in the form of phase-shifting material has been applied to the defect 520. The application of the phase-shifting material for producing a phase-shifting structure 1410 is explained below in the context of the discussion in relation to FIG. 16. In the example of FIG. 14, the phase-shifting structure 1410 comprises a layer whose thickness varies over the buried defect 520. The material of the phase-shifting structure 1410 has a refractive index at the actinic wavelength, the real part of said refractive index being as far away from 1 as possible, i.e. the real part of which is as small as possible. At the same time, the imaginary part of the refractive index should likewise be as small as possible such that the material of the phase-shifting structure 1410 only absorbs a small amount of the incident EUV radiation. A low absorption coefficient of the material of the phase-shifting structure 1410 is particularly expedient since the EUV radiation passes through the phase-shifting structure 1410 twice. Materials which currently come closest to this target are described in the context of the discussion relating to FIGS. 4 and 10.

The local thickness of the phase-shifting structure 1410 is determined in such a way that the local phase shift caused by the phase-shifting structure 1410 just compensates the local phase disturbance caused by the buried defect 520. The maximum thickness of the phase-shifting structure 1410 lies in the region of 100 nm. The material of the phase-shifting structure 1410 can be deposited down to a minimum thickness of approximately 1 nm.

The amplitude error of the buried defect 520 or the change in intensity caused by the defect 520 in the direction of the reflected radiation is repaired by a compensational repair. To this end, parts 1430, 1440 of the two pattern elements 1470 on both sides of the buried defect 520 are removed. The particle-beam-induced etching process carried out to this end is explained within the scope of the discussion relating to FIG. 16. When calculating the parts 1430, 1440 of the pattern elements 1470 to be removed, the absorption of the phase-shifting structure 1410 is also taken into account in addition to the amplitude error of the defect 520.

Determining the phase-shifting structure 1410 and determining the parts 1430, 1440 of the pattern elements 1470 to be removed is carried out within the scope of ascertaining a best-possible repair concept on the basis of simulations, as briefly explained in the context of the discussion relating to FIG. 3. The best-possible holistic repair concept is based on—as already explained above—a quantitative determination of the phase and intensity disturbance caused by the defect 520.

After the above-described repair steps, the phase error and the amplitude error of the buried defect 520 are corrected. This means that, after the repair has been carried out, the EUV mask 500 reflects substantially the same intensity from the region of the buried defect 520 as from an undisturbed part of the EUV mask 500. Moreover, the EUV radiation reflected from the region of the defect has the same form of the phase front as EUV radiation reflected by an undisturbed region of the EUV mask 500. However, the EUV radiation reflected from the repaired region of the EUV mask may have a fixed phase difference with respect to the phase front reflected from the undisturbed regions of the EUV mask 500 as a consequence of the phase-shifting structure 1410.

In order to remove this constant phase difference, a layer of phase-shifting material with a constant thickness 1420 is deposited over the region of the repaired defect 520. The layer thickness of the phase-shifting layer of constant thickness 1420 orients itself according to the fixed phase difference to be corrected. As already explained above, it is possible to produce layer thicknesses of the order of 1 nm. The maximum layer thickness of the phase-shifting layer of constant thickness 1420 is limited by the absorption coefficients of the material of the layer 1420. The maximum layer thickness of currently available phase-shifting materials is of the order of 100 nm. Here, it should be noted that the reflected EUV radiation passes through the phase-shifting layer of constant thickness 1420 twice.

The materials described above come into question as a material for the phase-shifting layer of constant thickness 1420. It is therefore possible to apply the phase-shifting structure 1410 and the phase-shifting layer of constant thickness 1420 with the same material composition over the defect 520 in one deposition process. Further, the absorption of the phase-shifting layer of constant thickness 1420 is likewise taken into account when determining the parts 1430, 1440 to be removed of the pattern elements 1470.

The sequence of the repair steps can be selected as desired. However, if a phase-shifting layer of constant thickness 1420 is applied over the buried defect 520 in addition to the phase-shifting structure 1410, it is expedient to correct the amplitude error of the defect 520 in the first step such that the phase-shifting layer of constant thickness 1420 can be guided right up to the edge of the modified pattern elements 1470.

Figure 15:
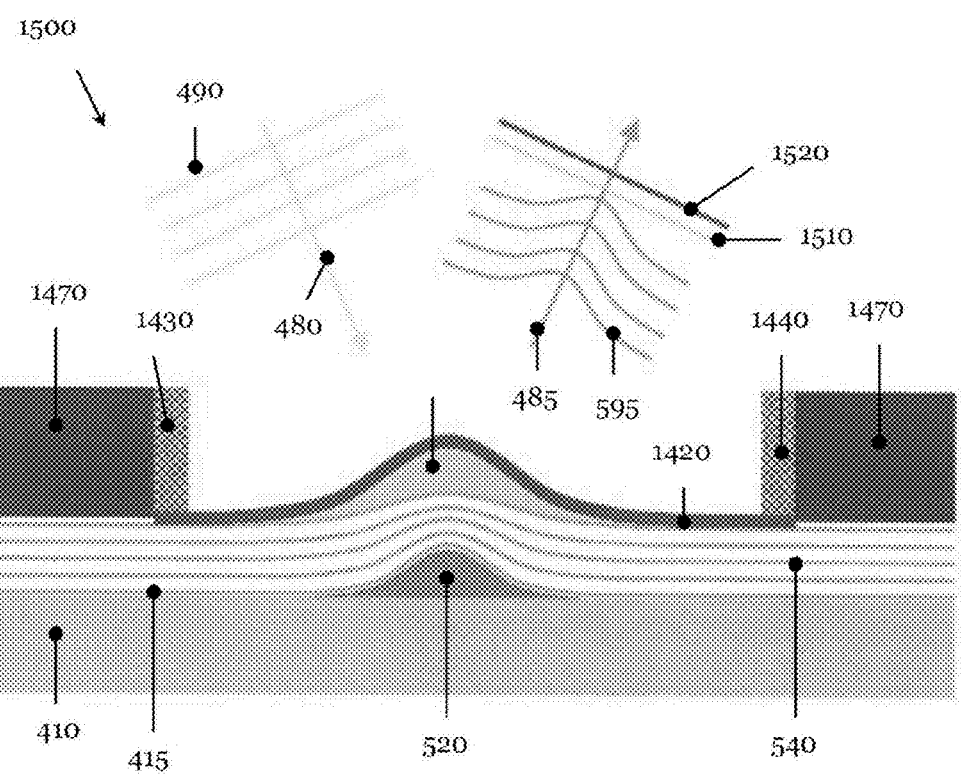
FIG. 15 represents the section of FIG. 14 and elucidates the effect of the repaired phase error on the phase front of the reflected EUV radiation.

FIG. 15 elucidates the effect of the repaired EUV mask 500. EUV radiation 480 with a plane phase front 490 impinges on the mask 500 at a defined angle. The EUV mask 500 reflects radiation 485 at an identical angle with respect to the perpendicular to the mask surface. Reference sign 595 denotes the phase distortion caused by the non-repaired defect 520, which is specified in FIG. 5. After correcting the buried defect 520, the EUV radiation reflected by the EUV mask 500 in the region of the corrected defect has a plane phase front 1510 again. A constant phase difference from the EUV radiation 1520 which is reflected from non-disturbed regions of the EUV mask 500 is corrected by the phase-shifting layer of constant thickness 1420.

Figure 16:
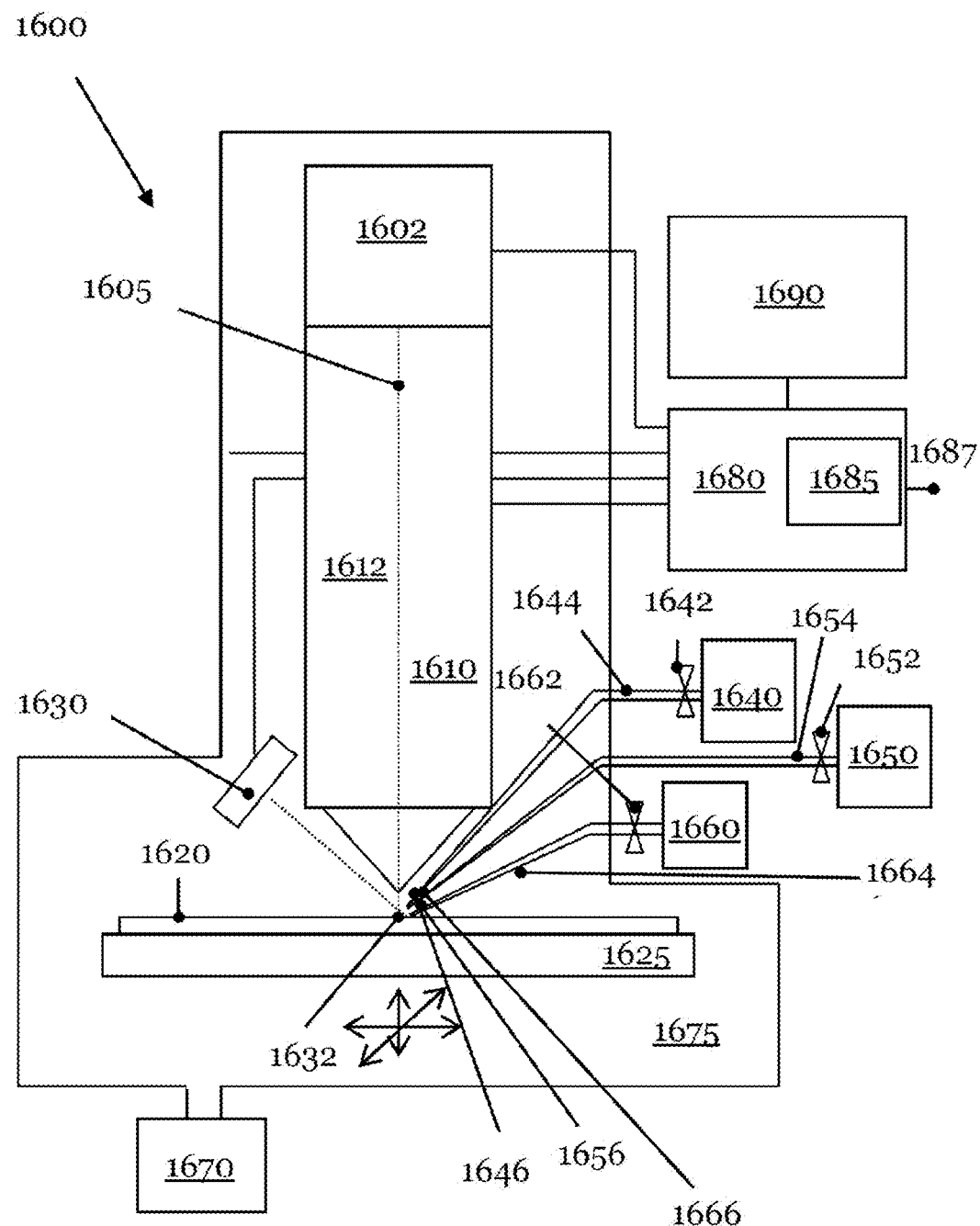
FIG. 16 schematically shows an apparatus which can be used to carry out the repair of buried defects of EUV masks.

FIG. 16 schematically shows a section through a few components of an apparatus 1600 that can be used to provide a phase-shifting structure 1410 and apply a phase-shifting layer of constant thickness 1420. Moreover, the apparatus 1600 can be used to modify one or more pattern elements 1470 of the EUV mask 500 (e.g., modify the parts 1430, 1440). The example illustrated in FIG. 16 presents a scanning particle microscope 1600 in the form of a scanning electron microscope (SEM) 1600. A particle beam 1605 in the form of an electron beam 1605 for repairing the buried defect 520 is advantageous in that the latter substantially cannot damage the EUV mask 1620 or it can only damage said EUV mask to a small extent. However, other charged particle beams are also possible, for example an ion beam of an FIB (Focused Ion Beam) system (not illustrated in FIG. 16).

The modified SEM 1600 comprises as essential components a particle gun 1602 and a column 1610, in which the electron optics or beam optics 1612 is arranged. The electron gun 1602 produces an electron beam 1605 and the electron or beam optics 1612 focuses the electron beam 1605 and directs it at the output of the column 1612 onto the EUV mask 1620, which may be identical to the EUV mask 500, 600 of FIGS. 5, 6 and 8 to 11.

The EUV mask 1620 is arranged on a specimen stage 1625. As symbolized in FIG. 16 by the arrows, the specimen stage 1625 can be moved in three spatial directions in relation to the electron beam 1605 of the SEM 1600.

The apparatus 1600 contains a detector 1630 for detecting the secondary electrons or backscattered electrons produced at the measurement point 1632 by the incident electron beam 1605. The detector 1630 is controlled by the control device 1680. Furthermore, the control device 1680 of the apparatus 1600 receives the measurement data of the detector 1630. The control device 1680 can generate images from the measurement data, said images being represented on a monitor 1690.

Moreover, the measurement apparatus 1600 may comprise an ion source which provides low-energy ions in the region of the measurement point 1632, said low-energy ions preventing the EUV mask 1620 or the surface thereof from having a negative surface charge (not illustrated in FIG. 16). With the aid of an ion source, it is possible to reduce a negative charge of the EUV mask 1620 in a local and controlled fashion and hence possible to prevent a reduction in the lateral spatial resolution of the electron beam 1620.

The electron beam 1605 of the apparatus 1600 can be used to analyze the defect 520 and, in particular, find the examined defect 520.

The control device 1680 comprises a computer system 1685. The computer system 1685 comprises an interface 1687. By way of this interface, it is possible to connect the computer system 1685 to the analysis unit 880 of the detection system 800 of the EUV-AIMS™ 1710 of subsequent FIG. 17 (not illustrated in FIG. 16). The computer system 1685 can receive measurement data via the interface 1687. In particular, the computer system 1685 can obtain measurement data of the buried defect 520 via the interface 1687, said measurement data having been recorded by use of one or more of the three measurement methods explained above. From these measurement data, the computer system 1685 is able to reconstruct the phase and intensity disturbance of the EUV mask 1620 emanating from the defect 520 in the region of the defect 520 and the reflected phase front 595, 1510, 1520. This means that the computer system 1680 can carry out a phase reconstruction algorithm. In an alternative embodiment, a phase reconstruction algorithm is carried out externally by the apparatus 1600 or the repair apparatus 1600 (see subsequent FIG. 17).

The computer system 1685 or the control unit 1680 further comprises a scanning unit which scans the electron beam 1605 over the EUV mask 1620. The scanning unit controls deflection elements in the column 1610 of the SEM 1600, which are not illustrated in FIG. 16. Further, the computer system 1685 or the control device 1680 comprises a setting unit, in order to set and control the various parameters of the SEM 1600. Parameters that can be set by the setting unit may be for example: the magnification, the focus of the electron beam 1605, one or more settings of the stigmator, the beam displacement, the position of the electron source and/or one or more stops (not illustrated in FIG. 16).

The apparatus 1600 for correcting a defect 520 and for ascertaining a best-possible repair concept for an examined defect 520 preferably comprises several different storage containers for various gases or precursor gases. Three storage containers 1640, 1650 and 1660 are illustrated in the exemplary apparatus 1600 of FIG. 16. However, an apparatus 1600 may also have more than three storage containers for processing an EUV mask 520, 1620.

The first storage container 1640 stores a precursor gas or a first deposition gas, which can be used in cooperation with the electron beam 1605 of the SEM 1600 for depositing material in the form of a phase-shifting structure 1410 on the defect 520 of the EUV mask 1620. By way of example, the first storage container 1640 may have a precursor gas in the form of a metal carbonyl, for example molybdenum hexacarbonyl ($Mo(CO)_6$).

The second storage container 1650 contains an etching gas, with the aid of which a part 1430 or a plurality of parts 1430, 1440 of one or more pattern elements 1470 can be etched from the surface of the multilayer structure 540 of the EUV mask 1620. By way of example, the second storage container 1650 may comprise xenon difluoride ($XeF_2$). Alternative etching gases which can be stored in the storage container 1650 are e.g. a halogen, for example fluorine ($F_2$) or chlorine ($Cl_2$) or a compound containing a halogen.

The third storage container 1660 stores a second deposition gas, with the aid of which a material of a phase-shifting layer of constant thickness 1420 can be deposited in the region of the buried defect 520 within the scope of a particle-beam-induced deposition reaction, e.g. with the aid of an electron beam 1605. By way of example, the third storage container may contain a metal carbonyl, e.g. dicobalt octacarbonyl ($Co_2(CO)_8$), dirhenium decacarbonyl ($Re_2(CO)_{10}$), nickel tetracarbonyl ($Ni(CO)_4$) or tungsten hexacarbonyl ($W(CO)_6$).

The second deposition gas may be identical to the first deposition gas. Therefore, in an alternative embodiment, the third storage container 1660 may contain a deposition gas by use of which a part or a plurality of parts of one or more pattern elements 1470 can be deposited on the multilayer structure 540 of the EUV mask 500, 1620. The third storage container 1660 may contain a metal carbonyl, e.g. chromium hexacarbonyl ($Cr(CO)_6$).

Each storage container 1640, 1650, 1660 is equipped with its own valve 1642, 1652, 1662 to control the amount of gas particles provided per unit of time or the gas flow rate at the location of incidence 1632 of the electron beam 1605 on the surface of the EUV mask 1620. Furthermore, the three storage containers 1640, 1650, 1660 have dedicated gas feeds 1644, 1654 and 1664, which end with a nozzle 1646, 1656 and 1666 near the point of incidence 1632 of the electron beam 1605 on the EUV mask 1620. In the apparatus 1600 that is illustrated by way of example in FIG. 16, the valves 1642, 1652, 1662 are installed in the vicinity of the storage containers 1640, 1650, 1660. In an alternative embodiment, the valves 1642, 1652, 1662 may be arranged in the vicinity of the corresponding nozzle 1646, 1656, 1666 (not shown in FIG. 16). Each storage container 1640, 1650, 1660 may have a dedicated element for the individual temperature setting and control. The temperature setting facilitates both cooling and heating for each gas. In addition, the gas feeds 1644, 1654, 1664 may likewise respectively have a dedicated element for setting and monitoring the temperature at which the gases are provided at the reaction location 1632 (likewise not shown in FIG. 16).

The apparatus 1600 of FIG. 16 may have a pump system 1670 to produce and maintain the required vacuum. In addition, the apparatus 1600 may include a suction extraction device (not illustrated in FIG. 16). The suction extraction device in combination with the pump system 1670 makes it possible that the fragments or constituents that are produced during the decomposition of a precursor gas, i.e. a deposition gas or an etching gas, and are not required for the local chemical reaction can substantially be extracted from the vacuum chamber 1675 of the apparatus 1600 at the point of origin. Since the gas constituents that are not required are pumped away locally at the point of incidence 1632 of the electron beam 1605 on the EUV mask 1620 out of the vacuum chamber 1675 of the apparatus 1600 before they can be distributed and settled in it, contamination of the vacuum chamber 1675 is prevented.

For initiating a local etching reaction or a local depositing process, preferably a focused electron beam 1605 is exclusively used in the apparatus 1600 that is given by way of example in FIG. 16. However, additionally or alternatively, it is also possible to initiate the local reaction(s) with the aid of a photon beam.

Figure 17:
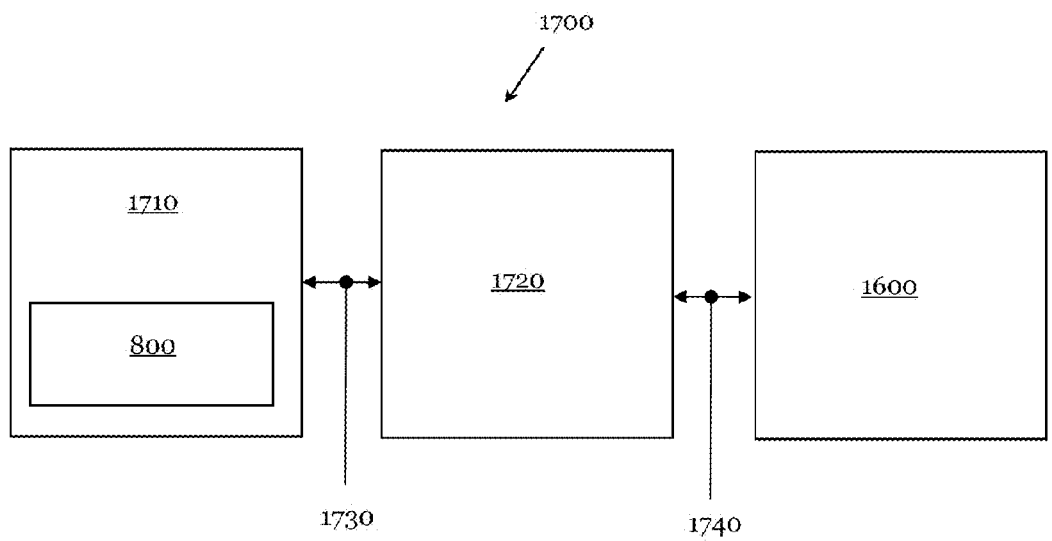
FIG. 17 schematically presents a system which combines an EUV-AIMS™ and the repair apparatus of FIG. 16.

The diagram 1700 of FIG. 17 schematically shows an exemplary combination of an EUV-AIMS™ 1710 with the repair apparatus 1600 from FIG. 16. The EUV-AIMS™ 1710 contains the detection system 800 of FIG. 8. In the example of FIG. 17, the EUV-AIMS™ 1710 is connected to a server 1720 by the connection 1730. By way of example, the server can be a mask repair center. The server 1720 can store the calibration data of the EUV-AIMS™ 1710 and of the repair apparatus 1600. Further, the server 1720 can contain the design data of the EUV mask 500 and a defect database. Furthermore, the server 1720 can comprise software for simulating aerial images. Moreover, the server 1720 can store one or more software programs which are designed to ascertain a repair concept for the buried defect 520.

In the example illustrated in FIG. 17, the EUV-AIMS™ 1710 receives calibration data via the connection 1730 and transmits measurement data to the server 1720 via the connection 1730.

Via its connector 1687, the repair apparatus 1600 is connected to the server 1720 by use of the connection 1740. Via the connection 1740, the server 1720 transmits a repair concept for the examined defect 520 to the repair apparatus 1600. Further, the server 1720 can receive measurement data from the repair apparatus via the connection 1740, for example the position of the examined defect, which was determined with the aid of the electron beam 1605 of the repair apparatus 1600.

The connections 1730 and 1740 can be electrical and/or optical signal lines.

In an alternative embodiment, the function of the server 1720 can be assumed by the EUV-AIMS™ 1710 or by the repair apparatus 1600. Further, it is possible to divide the function of the server 1720 among the EUV-AIMS™ 1710 and the repair apparatus 1600.

Figure 18:
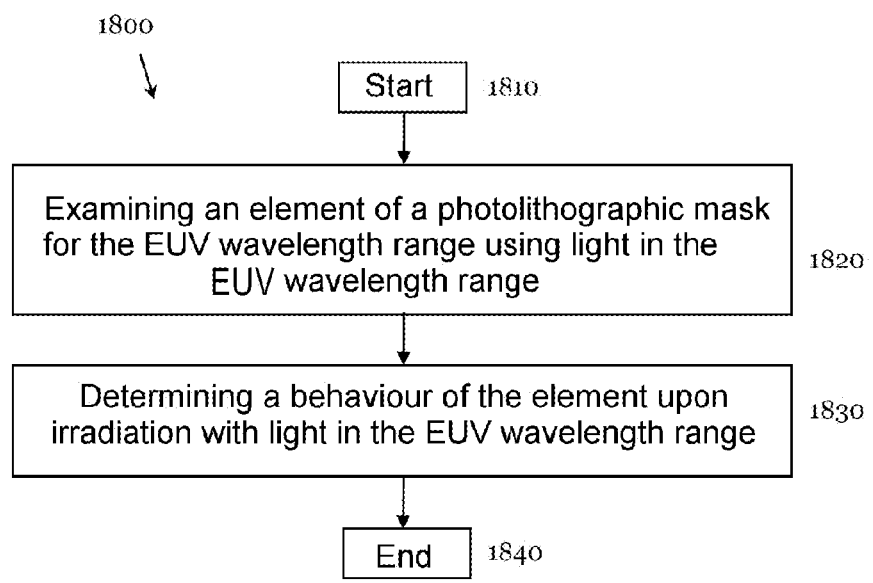
FIG. 18 indicates a flowchart of a method for examining an element of an EUV mask.

FIG. 18 presents a flowchart 1800 of an exemplary embodiment of the method, defined in this application, for examining a defect 520 of an EUV mask 500, 1620. The method begins in step 1810. In the first step 1820, an element of a photolithographic mask for the EUV wavelength range is examined with light from the EUV wavelength range. The EUV-AIMS™ 1710 of FIG. 18 can be used to examine the element. An element to be examined may comprise a defect, a critical point and/or a component of an EUV mask 500, 600, 1620. In the second step 1830, a behavior of the element upon irradiation with light in the EUV wavelength range is determined. If the examined element is a defect, use can be made of a phase reconstruction algorithm in order to determine the amplitude and phase error of the examined defect. The method ends at step 1840.

Figure 19:
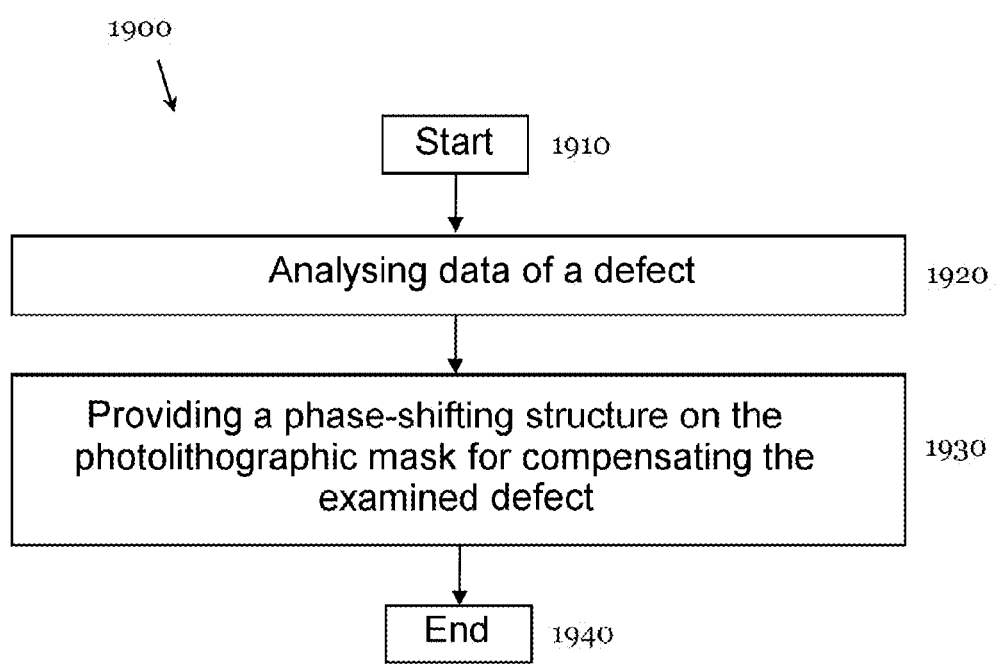
FIG. 19 finally illustrates a flowchart of a method for repairing a defect of an EUV mask.

Finally, FIG. 19 shows a flowchart 1900 of an exemplary embodiment of the method, defined in this application, for compensating a defect 520 of EUV masks 500, 1620. The method begins in step 1910. Data of a defect 520 are analyzed in the first step 1920. Analyzing data may include analyzing an available repair concept or analyzing measurement data for producing a repair concept. In the second step 1930, a phase-shifting structure 1410 is provided on the photolithographic mask 500, 1620 for compensating the examined defect 520. The phase-shifting structure 1410 can be deposited on the examined defect by use of the repair apparatus 1600. The method ends at step 1940.

In some implementations, the analysis unit 880 (FIG. 8), the computer system 1685 (FIG. 16), and the server 1720 (FIG. 17) can include one or more processors and one or more computer-readable media (e.g., RAM, ROM, SDRAM, hard disk, optical disk, and flash memory). The one or more processors can perform various calculations described above. The calculations can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., memory) and transmission media. Transmission media includes, without limitation, coaxial cables, copper wire, fiber optics and free space. The memory can include any type of memory, such as RAM, ROM, SDRAM, and flash memory.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., general purpose microprocessors, special purpose microprocessors, digital signal processors, single-core or multi-core processors, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, DVD-ROM, and Blu-ray BD-ROM disks. The processor and the memory can be supplemented by, or incorporated in, ASICs (application-specific integrated circuits).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Thus, particular embodiments of the subject matter have been described. Other embodiments are within the scope of the following claims. In some cases, the actions recited in the claims can be performed in a different order and still achieve desirable results.

What is claimed is:

1. A method for examining at least one element of a photolithographic mask for an extreme ultraviolet (EUV) wavelength range, wherein the method includes the steps of:
    (a) examining the at least one element with light in the EUV wavelength range, wherein the at least one element comprises at least one defect of a photolithographic mask;
    (b) wherein examining the at least one defect comprises controlled modifications of a phase of the light in the EUV wavelength range downstream of a reflection by the photolithographic mask to obtain a plurality of images of the at least one element with controlled wavefront modifications, in which different images are obtained with different controlled wavefront modifications; and
    (c) determining the behavior of the at least one element upon irradiation with light in the EUV wavelength range based on the plurality of images.

2. The method according to claim 1, wherein determining the behavior of the at least one element comprises: determining a phase change and/or an amplitude change which is caused by the at least one element upon the irradiation with light in the EUV wavelength range.

3. The method according to claim 1, wherein the controlled modification of the phase of the light in the EUV wavelength range comprises the introduction of a phase-shifting film into a beam path downstream of the reflection of the light by the photolithographic mask.

4. The method according to claim 3, wherein the introduction of a phase-shifting film into the beam path comprises: carrying out at least two measurements with phase-shifting films with different thicknesses.

5. The method according to claim 4, wherein determining the amplitude change and the phase change comprises: carrying out a recursive phase reconstruction algorithm with data from the at least two measurements.

6. The method according to claim 5, wherein the recursive phase reconstruction algorithm comprises at least one algorithm from the group including: an iterative Fourier ptychographic algorithm, an inverse Fourier transform algorithm, a Gerchberg-Saxton algorithm, an error reduction algorithm, a gradient method and a hybrid input-output algorithm.

7. The method according to claim 1, wherein examining the at least one defect comprises the steps of:
    (a) carrying out at least two measurements of the at least one defect under different incidence conditions of the light in the EUV wavelength range incident on the photolithographic mask; and
    (b) applying the recursive phase reconstruction algorithm to the data of the at least two measurements.

8. The method according to claim 7, wherein step a. comprises: carrying out at least two measurements of the defect at different angles using an at least partly coherent light source or inserting a monopole stop into the beam path upstream of the photolithographic mask and carrying out at least two measurements of the defect at different angles using an incoherent light source.

9. The method according to claim 1, wherein examining the at least one defect comprises the steps of:
    (a) carrying out at least two measurements of the at least one defect with different focal positions, and
    (b) applying the recursive phase reconstruction algorithm to the data of the at least two measurements.

10. The method according to claim 1, further including the steps of:
    (a) ascertaining a phase error and an amplitude error from the determined phase change and the determined amplitude change; and
    (b) ascertaining a repair concept for the at least one defect from the ascertained amplitude error and the ascertained phase error of the examined defect.

11. The method according to claim 1, further comprising the steps of:
    (a) analyzing data of the at least one defect; and
    (b) providing a phase-shifting structure on the photolithographic mask for compensating the examined defect.

12. The method according to claim 11, wherein providing the phase-shifting structure comprises: applying the phase-shifting structure on the examined defect for compensating a phase error of the examined defect.

13. The method according to claim 11, further including the step of: modifying at least one pattern element of the photolithographic mask for compensating an amplitude error of the examined defect.

14. The method according to claim 11, further including the step of: applying a phase-shifting layer of constant thickness in the region of the examined defect, wherein the thickness of the phase-shifting layer of constant thickness is selected such that a phase difference of the compensated defect in relation to a part of the photolithographic mask without a defect is compensated.

15. The method according to claim 1, further comprising the step of: analyzing a repair concept and/or ascertaining a repair concept from measurement data.

16. A non-transitory computer readable medium storing a computer program comprising instructions which, when executed by a computer system, prompt the computer system to carry out:
(a) examining the at least one element with light in the EUV wavelength range, wherein the at least one element comprises at least one defect of a photolithographic mask;
(b) wherein examining the at least one defect comprises controlled modifications of a phase of the light in the EUV wavelength range downstream of a reflection by the photolithographic mask to obtain a plurality of images of the at least one element with controlled wavefront modifications, in which different images are obtained with different controlled wavefront modifications; and
(c) determining the behavior of the at least one element upon irradiation with light in the EUV wavelength range based on the plurality of images.

17. An apparatus for examining at least one element of a photolithographic mask for an extreme ultraviolet (EUV) wavelength range, wherein the apparatus comprises:
(a) means for examining the at least one element with light in the EUV wavelength range, wherein the at least one element comprises at least one defect of a photolithographic mask;
(b) wherein examining the at least one defect comprises controlled modifications of a phase of the light in the EUV wavelength range downstream of a reflection by the photolithographic mask to obtain a plurality of images of the at least one element with controlled wavefront modifications, in which different images are obtained with different controlled wavefront modifications; and
(c) means for determining the behavior of the at least one element upon irradiation with light in the EUV wavelength range based on the plurality of images.

18. The apparatus according to claim 17, further comprising:
(a) means for analyzing data of the at least one defect; and
(b) means for providing a phase-shifting structure on the photolithographic mask for compensating the examined defect.

19. The apparatus according to claim 18, wherein the apparatus is configured to perform:
(a) examining the at least one element with light in the EUV wavelength range, wherein the at least one element comprises at least one defect of a photolithographic mask;
(b) wherein examining the at least one defect comprises a controlled modification of a phase of the light in the EUV wavelength range downstream of a reflection by the photolithographic mask; and
(c) determining the behavior of the at least one element upon irradiation with light in the EUV wavelength range.

20. The apparatus according to claim 17, wherein the apparatus is configured to carry out:
(a) examining the at least one element with light in the EUV wavelength range, wherein the at least one element comprises at least one defect of a photolithographic mask;
(b) wherein examining the at least one defect comprises a controlled modification of a phase of the light in the EUV wavelength range downstream of a reflection by the photolithographic mask; and
(c) determining the behavior of the at least one element upon irradiation with light in the EUV wavelength range.

* * * * *

UNITED STATES PATENT AND TRADEMARK OFFICE
CERTIFICATE OF CORRECTION

PATENT NO. : 10,386,297 B2
APPLICATION NO. : 15/838699
DATED : August 20, 2019
INVENTOR(S) : Jörg Frederik Blumrich and Johannes Ruoff It is certified that error appears in the above-identified patent and that said Letters Patent is hereby corrected as shown below:

In the Specification

Column 14
Line 53, delete "ZERODUIR®" and insert -- ZERODUR® --

Signed and Sealed this
Fifth Day of November, 2019

Andrei Iancu
*Director of the United States Patent and Trademark Office*